US012059560B2

(12) United States Patent
Kalita et al.

(10) Patent No.: US 12,059,560 B2
(45) Date of Patent: Aug. 13, 2024

(54) METHOD OF FORMING A DEVICE COMPRISING GRAPHENE

(71) Applicants: Centre National de la Recherche Scientifique, Paris (FR); UNIVERSITE GRENOBLE ALPES, Saint Martin d'Heres (FR)

(72) Inventors: Dipankar Kalita, Grenoble (FR); Vincent Bouchiat, Biviers (FR); Laetitia Marty, Quaix en Chartreuse (FR); Nedjma Bendiab, Grenoble (FR)

(73) Assignees: Centre National de la Recherche Scientifique, Paris (FR); Universite Grenoble Alpes, Saint Martin d'Heres (FR)

( * ) Notice: Subject to any disclaimer, the term of this patent is extended or adjusted under 35 U.S.C. 154(b) by 226 days.

(21) Appl. No.: 17/346,003

(22) Filed: Jun. 11, 2021

(65) Prior Publication Data

US 2021/0299436 A1     Sep. 30, 2021

Related U.S. Application Data

(63) Continuation-in-part of application No. 15/556,984, filed as application No. PCT/EP2016/054964 on Mar. 9, 2016, now Pat. No. 11,040,191.

(30) Foreign Application Priority Data

Mar. 9, 2015 (EP) ..................................... 15305351

(51) Int. Cl.
*A61N 1/04* (2006.01)
*A61L 15/58* (2006.01)
(Continued)

(52) U.S. Cl.
CPC ............ *A61N 1/0496* (2013.01); *A61L 15/58* (2013.01); *A61N 1/0468* (2013.01);
(Continued)

(58) Field of Classification Search
CPC ...... A61N 1/0468; A61N 1/0496; A61N 1/05; A61N 1/326; A61N 1/36046;
(Continued)

(56) References Cited

U.S. PATENT DOCUMENTS 7,945,302 B2   5/2011   McAdams
8,637,821 B2 * 1/2014   Buijsse ................ H01J 37/263
                                                    250/311

(Continued)

FOREIGN PATENT DOCUMENTS

CN         101048055       10/2007
CN         102920452 A      2/2013
(Continued)

OTHER PUBLICATIONS

Examiner Interview Summary Record (PTOL-413) Mailed on May 25, 2022 for U.S. Appl. No. 15/557,039.
(Continued)

*Primary Examiner* — Paul D Kim
(74) *Attorney, Agent, or Firm* — Maier & Maier, PLLC

(57) ABSTRACT

The invention concerns a method of forming a medical device, the method comprising: forming a graphene film (100) over a substrate (204); depositing, by gas phase deposition, a polymer material covering a surface of the graphene film (100); and removing the substrate (204) from the graphene film (100), wherein the polymer material forms a support (102) for the graphene film (100).

27 Claims, 9 Drawing Sheets

(51) Int. Cl.
 A61N 1/36 (2006.01)
 B05D 1/00 (2006.01)
 C01B 32/194 (2017.01)
 H01L 29/16 (2006.01)
 H01L 29/167 (2006.01)
(52) U.S. Cl.
 CPC ........... *A61N 1/36046* (2013.01); *B05D 1/60* (2013.01); *C01B 32/194* (2017.08); *H01L 29/1606* (2013.01); *H01L 29/167* (2013.01); *B05D 2203/30* (2013.01); *B05D 2518/00* (2013.01); *C01B 2204/04* (2013.01); *C01B 2204/22* (2013.01)
(58) Field of Classification Search
 CPC . C01B 32/186; C01B 32/194; C01B 2204/04; C01B 2204/22; H01L 29/1606; H01L 29/167; A61L 15/58; B05D 1/60; B05D 2518/00; B05D 2203/30
 See application file for complete search history.

(56) References Cited

U.S. PATENT DOCUMENTS

| | | | |
|---|---|---|---|
| 9,567,223 | B2 | 2/2017 | Song et al. |
| 9,890,043 | B2* | 2/2018 | Hersam .................. B01D 21/26 |
| 10,164,220 | B1 | 12/2018 | Lim et al. |
| 10,203,295 | B2* | 2/2019 | Swett ...................... G01N 25/72 |
| 2012/0103670 | A1 | 5/2012 | Lettow |
| 2012/0282419 | A1 | 11/2012 | Ahn et al. |
| 2013/0090542 | A1 | 4/2013 | Kipke et al. |
| 2013/0130037 | A1 | 5/2013 | Bol et al. |
| 2013/0285970 | A1 | 10/2013 | Ahn et al. |
| 2014/0010744 | A1 | 1/2014 | Ruona et al. |
| 2014/0145139 | A1 | 5/2014 | Huang et al. |
| 2014/0326700 | A1 | 11/2014 | Bouchiat et al. |
| 2014/0336597 | A1 | 11/2014 | Coulthard et al. |
| 2015/0098891 | A1 | 4/2015 | Song et al. |
| 2015/0343202 | A1 | 12/2015 | Picaud et al. |
| 2016/0169754 | A1 | 6/2016 | Kowalewski et al. |
| 2017/0057827 | A1 | 3/2017 | Sultana et al. |
| 2018/0056057 | A1 | 3/2018 | Kalita et al. |
| 2018/0057361 | A1 | 3/2018 | Kalita et al. |

FOREIGN PATENT DOCUMENTS

| | | |
|---|---|---|
| CN | 102925859 | 2/2013 |
| CN | 104000624 A | 8/2014 |
| EP | 2747158 A1 | 6/2014 |
| EP | 2778757 A1 | 9/2014 |
| JP | 2011-051801 A | 3/2011 |
| KR | 10-2014-0015927 A | 2/2014 |
| TW | M487718 U | 10/2014 |
| WO | 2013/116675 A1 | 8/2013 |
| WO | 2014/145139 | 9/2014 |
| WO | 2015/020610 A1 | 2/2015 |

OTHER PUBLICATIONS

Final Rejection Mailed on May 25, 2022 for U.S. Appl. No. 15/557,039.
Examiner Interview Summary Record (PTOL-413) Mailed on Jan. 21, 2022 for U.S. Appl. No. 15/557,039.
Non-Final Rejection Mailed on Sep. 24, 2021 for U.S. Appl. No. 15/557,039.
Office Action Appendix Mailed on Jan. 21, 2022 for U.S. Appl. No. 15/557,039.
Applicant Initiated Interview Summary (PTOL-413) Mailed on Sep. 29, 2020 for U.S. Appl. No. 15/556,984.
Applicant Initiated Interview Summary (PTOL-413) received for U.S. Appl. No. 15/557,039, mailed on Jun. 5, 2019, 3 pages.
Applicant Initiated Interview Summary received for U.S. Appl. No. 15/557,039, mailed on Sep. 11, 2019, 4 pages.
Authorized Officer: Cadamuro, Sergio, "International Search Report and Written Opinion" issued in PCT application No. PCT/EP2016/054964, dated May 10, 2016.
Authorized Officer: Follens, Lana, "International Search Report and Written Opinion" issued in PCT application No. PCT/EP2016/054963, dated Jun. 13, 2016.
English Translation of Office Action issued in Chinese Patent Application No. 201680026580.9 on Sep. 23, 2020.
Ex Parte Quayle Action Mailed on Jul. 9, 2020 for U.S. Appl. No. 15/556,984.
Examiner Interview Summary Record (PTOL-413) Mailed on Dec. 22, 2020 for U.S. Appl. No. 15/557,039.
Examiner Interview Summary Record (PTOL-413) Mailed on Sep. 29, 2020 for U.S. Appl. No. 15/556,984.
Final Office Action received for U.S. Appl. No. 15/557,039, mailed on Jan. 8, 2020, 19 pages.
Final Rejection Mailed on Mar. 31, 2021 for U.S. Appl. No. 15/557,039.
Final Rejection received for U.S. Appl. No. 15/557,039, mailed on Feb. 21, 2019, 16 pages.
G. C. Zografos et al., "Laser Doppler Flowmetry in Evaluation of Cutaneous Wound Blood flow ujsing Various Suturing Techniques", "Ann. Surg.", dated Mar. 1992, pp. 266-268, vol. 215, No. 3, Published in: GB.
Ivan Khrapach et al., "Novel Highly Conductive and Transparent Graphene-Based Conductors", dated 2012,DOI: 10.1002/adma.201200489, "Advanced Materials", pp. 2844-2849, vol. 24, Publisher: Wiley-VCH Verla GmbH & Co. KGaA, Weinheim.
Jian Zhang et al., "Electron Beam Lithography on Irregular Surfaces Using an Evaporated Resist", DOI: 10.1021/nn4064659, "ACS Nano", dated Mar. 26, 2014, pp. 3483-3489, vol. 8, No. 4, Publisher: American Chemical Society, Published in: CA.
Jiyoung Chang et al., "Facile electron-beam lithography technique for irregular and fragile substrates", doi: http://dx.doi.org/10.1063/1.4900505, "Applied Physics Letters", dated Oct. 1, 2014, vol. 105, No. 17.
Jung et al., KR 10-2014-0015927, Translation (Year: 2014).
L. C. Kloth, "Electrical Stinulation for Wound Healing: A Review of Evidence From In Vitro Studies, Animal Experiments, and Clinical Trials", XP055212717, ISSN: 1534-7346, DOI: 10.1177/1534734605275733, "The International Journal of Lower Extremity Wounds", dated Mar. 1, 2005, pp. 23-44, vol. 4, No. 1.
Luther C. Kloth, "Electrical StimulationTechnologies for Wound Healing", DOI: 10.1089/wound.2013.0459, "Advances in Wound Care", dated Mar. 8, 2013, pp. 81-90, vol. 3, No. 2, Publisher: Wound Healing Society.
Non-Final Office Action received for U.S. Appl. No. 15/556,984, mailed on Feb. 26, 2020, 13 pages.
Non-Final Rejection Mailed on Aug. 20, 2020 for U.S. Appl. No. 15/557,039.
Non-Final Rejection received for U.S. Appl. No. 15/557,039, mailed on Jul. 27, 2018, 15 pages.
Non-Final Rejection received for U.S. Appl. No. 15/557,039, mailed on Jun. 5, 2019, 17 pages.
Notice of Allowance and Fees Due (PTOL-85) Mailed on Feb. 10, 2021 for U.S. Appl. No. 15/556,984.
Notice of Allowance and Fees Due (PTOL-85) Mailed on Nov. 3, 2020 for U.S. Appl. No. 15/556,984.
Office Action Appendix Mailed on Dec. 22, 2020 for U.S. Appl. No. 15/557,039.
Office Action received for European Patent Application No. 15305351.7, mailed on Sep. 21, 2015, 12 pages.
Patricia Duran Ospina et al., "A Review in Innovation in Ocular Prostheses and Visual Implants:New Biomaterials and Neuro-Implants is the Challenge for the Visual Care", XP055212711, "Journal of Ocular Diseases and Therapeutics", dated Jul. 3, 2014, vol. 2, No. 9-16.
Requirement for Restriction/Election received for U.S. Appl. No. 15/556,984, mailed on Oct. 9, 2019, 7 pages.
Stan Monstrey et al., "Assessment of burn depth and burn wound healing potential", DOI: http://dx/doi.prg/10.1016/j.burns.2008.01.

(56) References Cited

OTHER PUBLICATIONS

009, "Burns", dated Sep. 1, 2008, pp. 761-769, vol. 34, No. 6, Publisher: Elsevier Inc., Published in: BE.

Tenhaeff et al., Initiated and Oxidative Chemical Vapor Deposition of Polymeric Thin Films: iCVD and oCVD, Apr. 18, 2008.

Wang Y et al., "Electrochemical delamination of CVD-grown graphene film: Toward the recyclable use of copper catalyst", XP002716759, ISSN: 1936-0851, DOI: 10.1021/NN203700W, "ACS Nano", dated Dec. 24, 2011, pp. 927-9933, vol. 5, No. 12, Publisher: American Chemical Society, Published in: US.

Xianrong Xing et al., "Electrochemical sensor based on molecularly imprinted film at polypyrrole-sulfonated graphene/hyaluronic acid-multiwalled carbon nanotubes modified electrode for determination of tryptamine", XP028353761, ISSN: 0956-5663, DOI: 10.1016/J.BIOS.2011.10.032, "Biosensors and Bioelectronics", dated Oct. 18, 2011, pp. 277-283, vol. 31, No. 1, Publisher: Elsevier BV, Published in: NL.

Zheng Han et al., "Homogeneous Optical and Electronic Properties of Graphene Due to the Suppression of Multilayer Patches During CVD on Copper Foils", dated 2013, DOI: 10.1002/adfm.201301732, "Advanced Functional Materials", pp. 1-7, Publisher: Wiley-VCH Verlag GmbH & Co. KGaA, Weinheim.

Clement Hébert et al., "Flexible Graphene Solution-Gated Field-Effect Transistors: Efficient Transducers for Micro-Electrocorticography", "Advanced Functional Materials", dated 2017, 15 pp., doi:10.1002/adfm.201703976.

Jonas Due Buron et al., "Electrically continuous graphene from single crystal copper verified by terahertz conductance spectroscopy and micro four-point probe". "Nano Letters", ACS Publications, Oct. 15, 2014, 24 pp., https://doi.org/10.1021/nl5028167.

Jonas D. Buron et al., "Graphene Conductance Uniformity Mapping", "Nano Letters", ACS Publications, Aug. 31, 2012, https://doi.org/10.1021/nl301551a.

Maria Kim et al., "Direct transfer of wafer-scale graphene films", "2D Materials", IOP Publishing, Jun. 22, 2017, 9 pp,m4 (2017) 035004, https:doi.org/10.1088/2053-1583/aa780d.

Pauline Ronseaux et al., "Highly flexible superconducting films with metal-decorated composite 2D materials", "Journal of Applied Physics", 126, 165301 (2019), published Oct. 22, 2019, 10 pp., https://doi.org/10.1063/1.152615.

Mohammad Mahdi Tavakoli et al., "Synergistic Roll-to-Roll Transfer and Doping of CVC-Graphene Using Parylene for Ambient-Stable and Ultra-Lightweight Photovoltaics", "Advanced Functional Materials", dated 2020, 11 pp., DOI: 10.1002/adfm.202001924.

Applicant Initiated Interview Summary (PTOL-413) Mailed on Sep. 3, 2020 for U.S. Appl. No. 15/557,039.

Notice of Allowance Mailed on May 19, 2021 for U.S. Appl. No. 15/556,984.

* cited by examiner

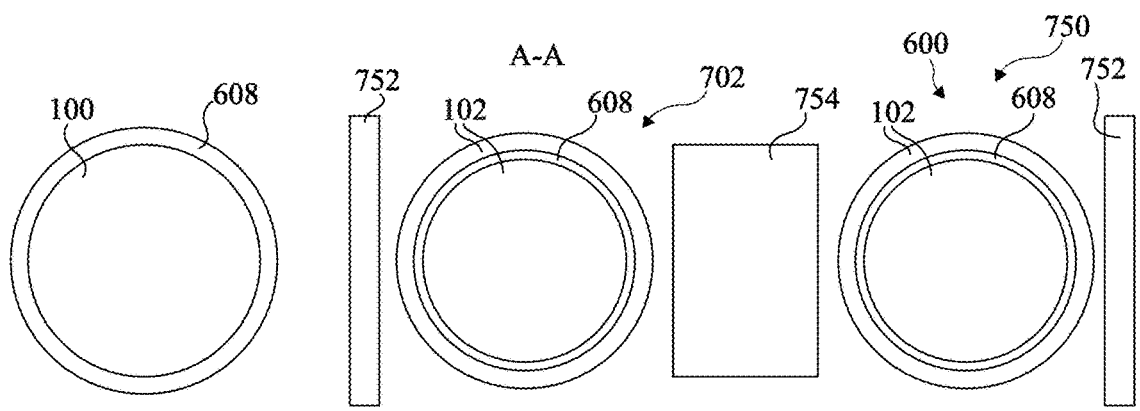
Fig 6B
Fig 7C
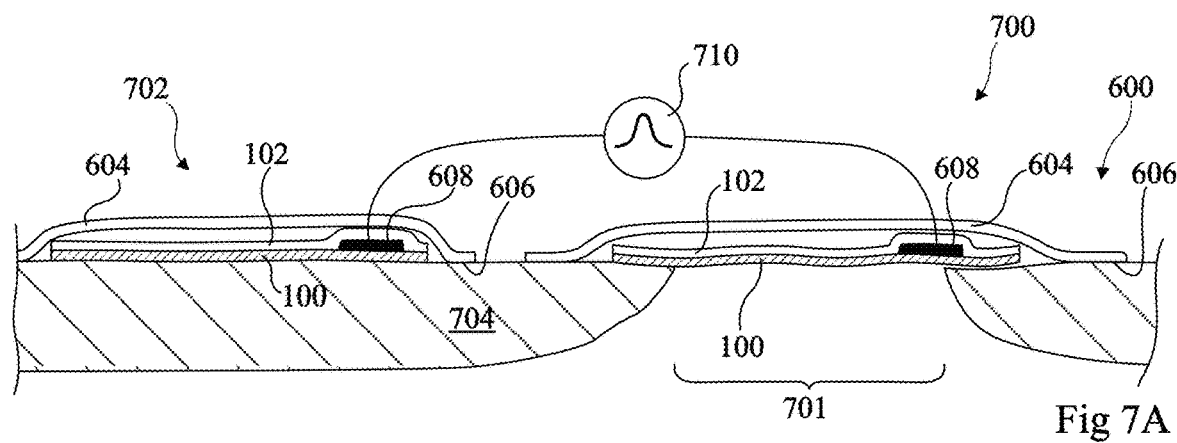
Fig 7A
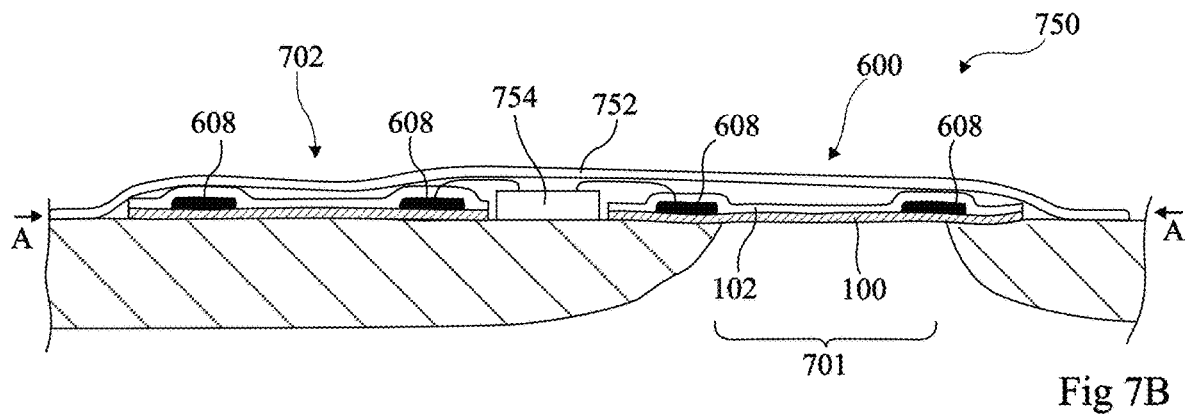
Fig 7B
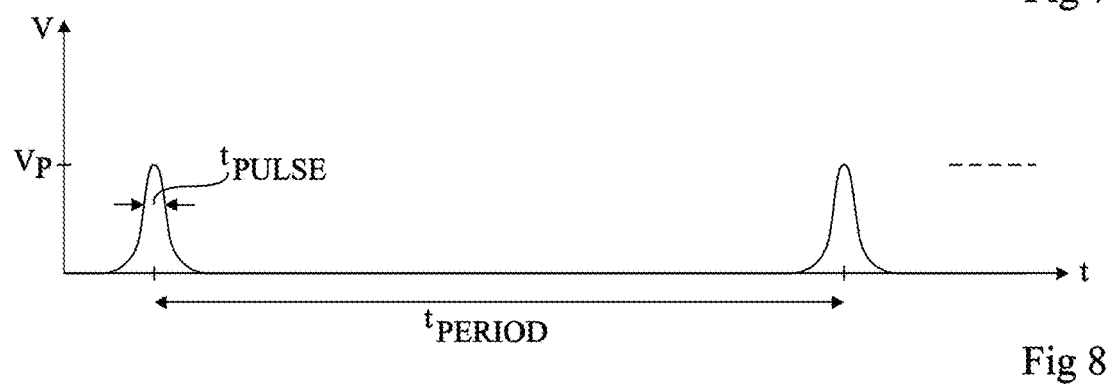
Fig 8

METHOD OF FORMING A DEVICE COMPRISING GRAPHENE

RELATED APPLICATIONS

The present patent application is a continuation-in-part of U.S. patent application Ser. No. 15/556,984, now U.S. Pat. No. 11,040,191, which is a 371 of International application PCT/EP2016/054964, which claims the priority benefit of European patent application EP 15305351.7, the entire disclosures of which are incorporated herein by reference.

FIELD

The present invention relates to the field of devices comprising a conductive layer, and to a method of forming such a device. In a preferred embodiment the present invention relates to the field of medical devices comprising a conductive layer, and to a method of forming a medical device comprising a conductive layer.

BACKGROUND

Graphene is a substance composed of carbon atoms forming a crystal lattice one atom in thickness. Various applications have been proposed for graphene, including its use in radio-frequency transistors and for forming transparent highly conductive and flexible electrodes, such as for displays. It is of particular benefit in applications where high mobility conductors are desired. Most applications of graphene require a macroscale-sized graphene layer, comprising one or a few layers of carbon atoms, which is transferred onto a substrate of a material selected based on the particular application.

Graphene is generally formed using a chemical vapor deposition (CVD) process, wherein graphene is deposited over a base substrate such as a copper foil.

However, a difficulty is that it is relatively difficult to remove the graphene layer from the base substrate without damaging or polluting the graphene layer and/or degrading its conductivity. Furthermore, in some embodiments it would be desirable to provide a method of forming a three-dimensional (3D) graphene device.

There is thus a need in the art for an improved method of forming a graphene device, and to one or more graphene devices formed based on such a method.

Certain types of devices are designed to form a conductive interface with any surface. More particularly, certain types of medical devices are designed to form a conductive interface with a human or animal body.

Hébert et al ("Flexible graphene solution-gated field-effect transistors: efficient transducers for micro-electrocorticography", *Adv. Funct. Mater.* 2017, doi: 10.1002/adfm.201703976} describes characteristics of a device comprising a graphene layer usable for neural interfacing, wherein said device is prepared by a process comprising a transfer of a graphene layer from the growth substrate onto the polymer.

For example, certain types of medical patches may comprise a conductive layer held against the skin of a human or animal, and a wire for monitoring an electrical signal on the conductive layer.

As a further example, an ophthalmic element may be positioned on the surface of the eye of a human or animal, and use a conductive layer to shield the eye, or monitor certain properties of the eye.

As yet a further example, a medical implant is a needle-like element that can be inserted into tissue of a human or animal body and comprises an electrically conductive portion allowing electrical signals to be monitored.

Such medical devices should generally comprise a conductive portion with good electrical conductivity, and be capable of maintaining close electrical contact with the skin or tissue of the human or animal body. However, existing devices tend not to be able to sufficiently meet both of these needs simultaneously.

Furthermore, such medical devices often use metal layers which are susceptible to oxidization.

SUMMARY

It is an aim of embodiments of the present disclosure to at least partially address one or more needs in the prior art.

According to one aspect, there is provided a method of forming a device comprising a graphene layer, the method comprising:
  forming a graphene layer over a substrate;
  depositing, by gas phase deposition, a polymer material covering a surface of the graphene film; and
  removing the substrate from the graphene layer, wherein the polymer material forms a support for said graphene layer.

In a preferred embodiment, the present invention provides a method of forming a medical device comprising a graphene layer.

According to another aspect, there is provided a device comprising a graphene layer, wherein said device is obtained by a method according to the invention, said method comprising the steps of:
  forming a graphene layer over a substrate;
  depositing, by gas phase deposition, a polymer material covering a surface of the graphene film; and
  removing the substrate from the graphene layer, wherein the polymer material forms a support for said graphene layer.

The present invention therefore provides a method of forming a device, and preferably a medical device, comprising a conductive graphene layer; the present invention also provides a device, and preferably a medical device comprising a conductive graphene layer.

A particular advantage of a method according to the invention resides in that, as the final polymer substrate is directly deposited by CVD onto the graphene film layered on the substrate, said method does not require the prior art commonly used liquid transfer technique of graphene on the substrate, which involves a liquid transfer of graphene/polymer films. A direct consequence of the absence of said liquid transfer step in a method of the present invention is the reproducibility and high scalability of a method and a device according to the invention.

Another particular advantage of a method according to the invention resides in that, due to the absence of said liquid transfer technique of graphene on the substrate, the surface of the graphene which is finally exposed and used for electrical testing and interfacing, in a device obtained by a method of the invention, i.e. the "exposed surface of graphene", is the surface of the graphene film which was in contact with the initial substrate. The exposed surface of graphene is the one that was in contact with the substrate, in particular a metallic substrate, and not with a polymer. The quality of said exposed surface is essential for further use of said device, for example for interface of a medical device with human or animal body.

As a consequence, the exposed surface of graphene, in a device of the present invention, is free from any contaminant. More particularly, in a device according to the invention the exposed surface of graphene is free from any polymer contaminant, no particular cleaning of the exposed graphene surface is required.

On the contrary, in methods and devices of prior art, the exposed surface of graphene is in contact with the polymer during its fabrication. The high density of polymer residual in devices of prior art involves performing a further cleaning step, which imposes harsh treatments susceptible to be incompatible with polymer film of devices, in particular with polymer films of medical device.

A third advantage of a method and a device according to the present invention is that it is cost-effective, as it enables easy industrial upscaling that reduces cost by removing the need for manual handling of graphene and enabling roll-to-roll processing of bulk quantities. The graphene transfer step of methods of prior art represents a major issue, which prevents graphene to reach large industrial market. A method and a device according to the present invention totally overcome this issue.

The present invention provides a conductive device comprising: a graphene film and a layer of polymer material covering a surface of the graphene film, wherein the polymer material forms a support for the graphene film, wherein said conductive device is characterized by a density of particulate contamination inferior to one contaminant per 10 square micron area of the exposed surface of said graphene film.

In a particular embodiment, a conductive device of the present invention is characterized by a charge neutrality point inferior to 0.2 V.

In another particular embodiment, a conductive device of the present invention is characterized by an electronic mobility superior to 800 cm2(V·s)-1.

In another particular embodiment, a conductive device of the present invention is characterized by a resistivity, for a sample of 1 cm$^2$, is characterized by a square resistance inferior to 10 kilo Ohm/square, preferably inferior to 7 kilo Ohm/square, more preferably comprised between 0.5 and 5 k Ohm/square.

A device according to the present invention exhibits highly important characteristics:
- a very low impurity density on the exposed surface of graphene, very few impurities are present with density of particulate contamination inferior to one contaminant per area of 10 square microns. The absence of any contaminant on the exposed surface of a graphene film in a device according to the invention is illustrated in FIGS. 12A and 13A,
- a charge neutrality point inferior to 0.2 V, preferably comprised between −0.1 and 0.1 Volt and very close to 0 Volts,
- an electronic mobility above 800 cm2(V·s)-1, preferably above 900 cm2(V·s)-1, more preferably above 1000 cm2(V·s)-1, as shown in transconductance curves obtained by electrostatic field effect assessing for the 5 good cristalline quality of graphene,
- An average value and spread of the resistivity well below prior art devices, said resistivity measured for one centimeter long samples being inferior to 10 kilo Ohm/square, preferably inferior to 7 kilo Ohm/square, more preferably comprised between 0.5 and 5 kOhms/square.

A comparative illustration of a process of the present invention and of a process prior art is shown in FIGS. 12A and 12B, respectively. An illustrative picture of a device according to the invention is shown in FIG. 13.

According to one embodiment, a device according to the invention further comprises at least one electrode electrically coupled to the layer of graphene. More particularly, a device according to the invention comprises one or two electrodes electrically coupled to the layer of graphene.

According to one embodiment, a device according to the invention further comprises at least one wire contact electrically coupled to the layer of graphene.

More particularly, a device according to the invention further comprises one or two wire contacts electrically coupled to the layer of graphene.

According to one embodiment, in a device according to the invention the thickness of the graphene film is from one atom to 8 atom layers.

According to one embodiment, in a device according to the invention the graphene film is doped in order to reduce its surface resistance.

More particularly, in a device according to the invention the graphene film is doped with P-dopants. In particular, said dopants are preferably chosen among AuCl3 and HNO3.

According to one embodiment, in a device according to the invention layers of FeCl3 are intercalated between one or more of the graphene layers.

According to one embodiment, the polymer material comprises a polymer from the n-xylylene family.

According to one embodiment, the polymer material comprises parylene.

According to one embodiment, the polymer layer is deposited with a thickness of between 10 nm and 5 mm.

According to one embodiment, the graphene film is formed over a three-dimensional surface of the substrate.

According to one embodiment, removing the substrate from the graphene film is performed by a process of electrochemical delamination or using an acid etch.

According to one embodiment, the method is for forming a sensor device to be placed over a three-dimensional form, wherein: the substrate on which the graphene film is formed comprises a mold having the shape of the three-dimensional form.

According to one embodiment, the mold is formed of a first material and at least one zone of a second material; during the formation of the graphene film, graphene selectively forms on the at least one zone of the second material and not on the first material; and the polymer material is deposited over the graphene film and at least a portion of the first material.

According to one embodiment, the method further comprises, after removing the substrate from the graphene film, performing a further gas phase deposition of the polymer material to encapsulate the graphene film.

According to one embodiment, the graphene film is deposited to form a conductive track having a meandering form in a detection zone.

According to one embodiment, the graphene film is deposited in the form of a first plate of graphene formed in a detection zone and connected to a first conductive track, and the method further comprises: forming a further graphene film covered by a further deposition of polymer material, wherein the further graphene film is deposited in the form of a second plate of graphene; and assembling the first and second graphene films such that the first and second graphene plates form a capacitive interface in the detection zone separated by a layer of the polymer material.

According to a further aspect, there is provided a sensor device comprising: a graphene film covered on at least one side by a polymer material having, on a portion of its inside surface, a detection element formed of a graphene film, the polymer material contacting with and supporting the graphene film.

According to one embodiment, the detection element comprises a meandering conductive track formed in a detection zone and electrically connecting a first conductive track to a second conductive track.

According to one embodiment, the detection element comprises first and second graphene plates at least partially overlapping each other, the first graphene plate being connected to a first conductive track, and the second graphene plate being connected to a second conductive track. According to one embodiment, the graphene device further comprises a detection circuit coupled to the first and second conductive tracks.

According to a preferred aspect of the present invention, there is provided a method of forming a medical device, the method comprising: forming a graphene film over a substrate; depositing, by gas phase deposition, a polymer material covering a surface of the graphene film; and removing the substrate from the graphene film, wherein the polymer material forms a support for the graphene film.

According to one embodiment, the method is for forming a conductive medical patch, the method further comprising: providing an adhesive band covering the polymer support and suitable for holding the graphene film in contact with a body; and electrically coupling a wire contact to the graphene film.

According to one embodiment, electrically coupling the wire contact to the graphene film comprises, prior to depositing the polymer material, forming the wire contact on the surface of the graphene film, wherein depositing the polymer material comprises coating the wire contact with the polymer material.

According to one embodiment, a conductive device of the invention is a conductive medical device.

According to a more particular embodiment, a conductive device of the invention is a conductive medical device chosen among a conductive medical patch, a wound treatment apparatus, an ophthalmic element, an eye protection device and an implant.

According to one embodiment, the method further comprises forming a conductive electrode patch of the conductive medical patch and a current supply circuit, the current supply circuit being adapted to apply a current between the graphene film and the conductive electrode patch, wherein the adhesive band is also suitable for holding the conductive electrode patch in contact with the body. According to one embodiment, the method further comprises forming two conductive electrodes patches of the conductive medical patch and a current supply circuit, the current supply circuit being adapted to apply a current between said two electrode patches within the graphene film, wherein said current is longitudinally applied within said graphene film, and wherein the adhesive band is configured to hold the conductive electrode patches in contact with the body.

According to one embodiment, the conductive medical device is a conductive medical patch comprising:
  a graphene film;
  a support for the graphene film, the support comprising the polymer material covering the surface of the graphene film;
  an adhesive band covering the support, the adhesive band for and holding the graphene film in contact with a body of an animal or a human, wherein the adhesive layer is removable from the body and
  at least one wire contact electrically coupled to the graphene film, particularly one or two wire contacts electrically coupled to the graphene film.

According to one embodiment, the conductive medical patch is a transparent hydrocolloidal dressing, the graphene film forming an external surface for contact with a wound, and the polymer material being a porous layer positioned between the graphene film and a pad formed of a hydrocolloid.

According to one embodiment, the conductive medical device is a wound treatment apparatus comprising a conductive medical patch placed over the wound; said conductive medical patch comprising:
  the graphene film;
  the support for the graphene film, the support comprising the layer of polymer material covering the surface of the graphene film,
  the adhesive band covering the support, the adhesive band for and holding the graphene film in contact with the body of the animal or the human, wherein the adhesive band is removable from the body,
  two electrodes electrically coupled to the graphene film, and
  a voltage application module adapted to apply voltage pulses between the first and second electrode of said conductive medical patch.

According to another embodiment, the conductive medical device is a wound treatment apparatus comprising a first and a second conductive medical patches, one of the first and second conductive medical patches for placing over the wound; each of the conductive medical patches comprising:
  the graphene film;
  the support for the graphene film, the support comprising the layer of polymer material covering the surface of the graphene film,
  the adhesive band covering the support, the adhesive band for and holding the graphene film in contact with the body of the animal or the human, wherein the adhesive band is removable from the body,
  a wire contact electrically coupled to the graphene film, and
  a voltage application module adapted to apply voltage pulses between the first and second conductive medical patches.

According to another embodiment, the conductive medical device is a wound treatment apparatus comprising a conductive medical patch placed over the wound and a further electrode, designed as a "counter electrode"; said conductive medical patch comprising:
  the graphene film;
  the support for the graphene film, the support comprising the layer of polymer material covering the surface of the graphene film,
  the adhesive band covering the support, the adhesive band for and holding the graphene film in contact with the body of the animal or the human, wherein the adhesive band is removable from the body,
  a first and a second electrode electrically coupled to the graphene film, and
  a voltage application module adapted to apply voltage pulses between the first and second electrode of said conductive medical patch,
wherein said counter electrode being placed at a distance of approximately 10 cm from said conductive medical patch.

According to one embodiment, the wound treatment apparatus further comprises a current sensor and/or voltage sensor for detecting the current and/or voltage applied between the wound dressing and the electrode patch.

According to one embodiment, the wound treatment apparatus further comprises a pulse generator for detecting the current and/or voltage applied between the wound dressing and the electrode patch.

According to one embodiment, the method is for forming an ophthalmic element, the substrate on which the graphene film is formed having a curved surface having a shape compatible with the surface of an eye.

According to one embodiment, a surface of the substrate on which the graphene film is formed comprises a pattern of first and second materials, the first material and not the second material supporting graphene formation, the method comprising selectively forming said graphene film over said first material and not over said second material.

According to one embodiment, the method is for forming an implant, wherein the substrate on which the graphene film is formed is a mold having an inner surface having the form of the implant, and wherein after the graphene film has been deposited on the inner surface of the mold, the mold is filled by the polymer material to form a polymer core of the implant that supports the graphene film.

According to one embodiment, a portion of the mold is not removed such that it remains in contact with the graphene film and forms an electrode of the implant.

According to one embodiment, the polymer material is deposited over the graphene film in a layer of between 5 and 40 nm in thickness.

According to a further aspect, there is provided a conductive medical patch comprising: a graphene film covered by a layer of a polymer material; and a wire contact electrically coupled to the layer of graphene.

According to a further aspect, there is provided a conductive medical patch comprising: a graphene film covered by a layer of a polymer material; and at least one, preferably two, wire contacts electrically coupled to the layer of graphene.

According to one embodiment, the graphene film is capable of contact with a body to which the patch is to be applied, the conductive patch further comprising an adhesive layer especially designed for holding the graphene film in contact with the body, wherein the adhesive layer is capable of being removed from the body leaving at least part of the graphene film in place.

According to one embodiment, the polymer material comprises hyaluronic acid.

According to one embodiment, the conductive medical patch is a hydrocolloidal dressing, the graphene film forming an external surface for contact with wound, and the polymer material being a porous layer positioned between the graphene film and a pad formed of a hydrocolloid.

According to a further aspect, there is provided a wound treatment apparatus comprising: the above conductive medical patch for placing over the wound; a further conductive patch; and a voltage application module adapted to apply voltage pulses between the conductive medical patch and the further conductive patch.

According to a further aspect, there is provided an ophthalmic element comprising: a curved plate formed of a graphene film covered by an outer layer of polymer material.

According to a further aspect, there is provided an eye protection device comprising the above ophthalmic element, wherein the graphene film forms a continuous layer across the element.

According to a further aspect, there is provided an implant comprising: a core in the form of a shaft having a pointed end and formed of a polymer material; and a graphene film covering and supported by the polymer core.

BRIEF DESCRIPTION OF THE DRAWINGS

The foregoing and other features and advantages will become apparent from the following detailed description of embodiments, given by way of illustration and not limitation with reference to the accompanying drawings, in which:

FIG. 6B is a plan view of a graphene film and contact electrode according to an example embodiment of the present disclosure;

FIG. 7A is a cross-section view of a wound treatment apparatus comprising the medical patch of FIG. 6A according to an example embodiment;

FIG. 7B is a cross-section view of a medical patch having a wound dressing and contact electrode according to an example embodiment;

FIG. 7C illustrates a view of the medical patch of FIG. 7B taken in a plane A-A of FIG. 7B;

FIG. 8 is a timing diagram illustrating a voltage signal applied by the apparatus of FIG. 7A according to an example embodiment.

For ease of illustration, the various figures are not drawn to scale.

DETAILED DESCRIPTION

Figure 1:
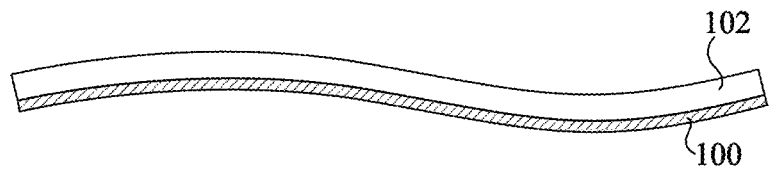
FIG. 1 is a cross-section view of a graphene device according to an example embodiment of the present disclosure.

FIG. 1 is a cross-section view of a graphene device comprising a film 100 of graphene, which is for example just one atom in thickness, or may have a thickness of up to 8 or more atom layers in some embodiments, depending on the application and the desired electrical conductivity. In particular, the graphene film 100 is for example formed of one or a plurality of graphene mono-layers attached together. In some embodiments, the graphene film 100 is doped in order to reduce its surface resistance, for example using P-dopants such as AUCl3 and/or HNO3. Additionally, or alternatively, layers of FeCl3 may be intercalated between one or more of the graphene layers to reduce the element resistance. For example, such a technique is described in more detail in the publication entitled "Novel Highly Conductive and Transparent Graphene-Based Conductors", I. Khrapach et al, Advanced Materials 2012, 24, 2844-2849, the contents of which is hereby incorporated by reference.

In plan view (not represented in FIG. 1), the graphene film 100 may have any shape, and for example has a surface area of anywhere between 1 µm2 and 200 cm$^2$, depending on application.

The graphene film 100 is covered by a support 102 in the form of a layer of polymer material. The polymer material is for example selected from the family of n-xylylenes, and in one example comprises parylene. Parylene has the advantage of being capable of being stretch by up to 200% before breaking, and is capable of remaining flexible over a relatively wide temperature range. In one example, the polymer material comprises parylene C or parylene N. Both parylene C and parylene N have the advantage of being relative elastic, while parylene N has a slightly lower Young's modulus, and thus a higher elasticity, than parylene C.

As will be described in more detail below, the polymer support 102 has for example been formed by a gas phase deposition technique or by a spin deposition technique. The polymer support 102 for example has a thickness of between 10 nm and a few tens or hundreds of µm, depending on the application. In some embodiments, the thickness of the polymer support 102 could be as low as 5 nm, and for example in the range 5 to 40 nm.

While in the example of FIG. 1 the polymer support is in the form of a layer having a substantially uniform thickness, as will become apparent from the embodiments described below, the polymer support could take other forms depending on the particular application.

The combination of a graphene film 100 and a polymer support 102 provides a multi-layer that can have relatively high electrical conductance while remaining flexible and strong. Of course, while the multi-layer of FIG. 1 has just two layers—the graphene layer and the parylene layer that form a bi-layer, in alternative embodiments there could be one or more further layers. For example, the graphene layer could be sandwiched by parylene layers on each side, and/or one or more layers of further materials could be formed in contact with the graphene or parylene layer.

Furthermore, the use of a polymer such as parylene leads to a device that is biocompatible, making the device suitable for a variety of medical or physiological applications in which it can for example contact human or animal tissue. The term medical device is used herein to cover any device suitable for close contact with human or animal tissue for the purpose of protection, treatment, diagnosis, or any other purpose.

Figure 2:
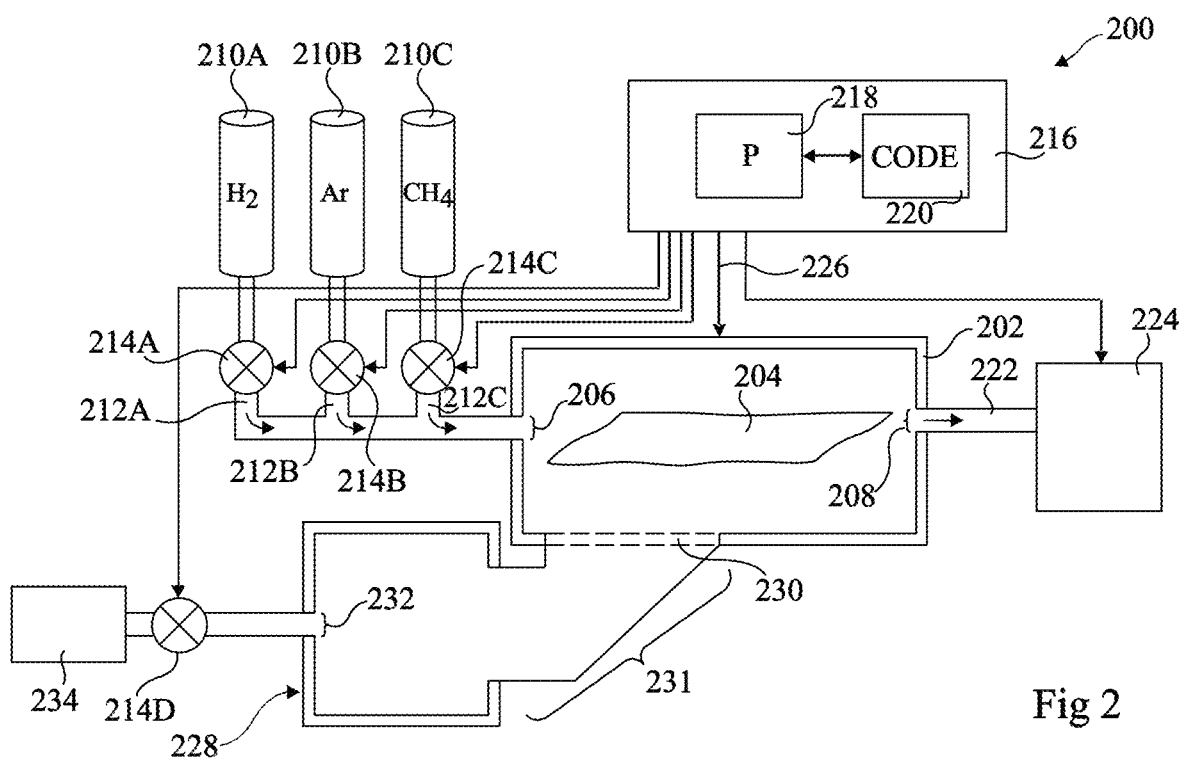
FIG. 2 schematically illustrates an apparatus for forming a graphene device according to an example embodiment of the present disclosure.

FIG. 2 illustrates apparatus 200 for forming a graphene device such as the device of FIG. 1 according to an example embodiment.

The step of forming the graphene film 100 for example involves forming mono-layers of graphene using the apparatus 200. A similar apparatus is described in the publication entitled "Homogeneous Optical and Electronic Properties of Graphene Due to the Suppression of Multilayer Patches During CVD on Copper Foils", Z. Han et al., Adv. Funct. Mater., 2013, DOI: 10.1002/adfm.201301732, and in the US patent application published as US2014/0326700. The contents of these documents is hereby incorporated by reference to the extent permitted by the law.

The apparatus 200 comprises a reaction chamber 202 in which the graphene film is formed. For example, the reaction chamber 202 is a tube furnace or other type of chamber that can be heated.

A substrate 204, for example formed of a foil of copper or another material and having a thickness of between 0.1 and 100 µm, is placed within the chamber 202. The substrate 204 provides a surface suitable for graphene formation. In particular, the material of the substrate 204 is for example selected as one that provides a catalyst for graphene formation, and for example has relatively low carbon solubility. For example, other possible materials for forming the substrate 204 include other metals such as nickel, cobalt, or ruthenium or copper alloys such as alloys of copper and nickel, copper and cobalt, copper and ruthenium, or dielectric materials, such as zirconium dioxide, hafnium oxide, boron nitride and aluminum oxide. In some embodiments, rather than being a foil, the substrate 204 could have a 3D form having at least one of its dimensions in the range 0.1 μm to tens or hundreds of μm. Such a 3D substrate could be formed of a material suitable for graphene formation, or it could be formed of another material and have a coating, of a material suitable for graphene growth, over at least part of its surface. Furthermore, the substrate 204 could be formed on a planar or 3D surface of a further substrate, for example of copper or another material such as sapphire.

An inlet 206 of the reaction chamber 202 allows gases to be introduced into the chamber, and an outlet 208 allows gases to be extracted from the chamber. The inlet 206 is for example supplied with gas by three gas reservoirs 210A, 210B and 210C, which in the example of FIG. 2 respectively store hydrogen ($H_2$), argon (Ar), and methane (CH4). In alternative embodiments discussed in more detail below, different gases could be used. In particular, rather than hydrogen, a different etching gas, in other words one that is reactive with carbon, could be used, such as oxygen. Rather than argon, another inert gas could be used, such as helium. This gas is for example used to control the overall pressure in the reaction chamber 202, and could be omitted entirely in some embodiments. Rather than methane, a different organic compound gas could be used, such as butane, ethylene or acetylene.

The inlet 206 is coupled to: reservoir 210A via a tube 212A comprising a valve 214A; reservoir 210B via a tube 212B comprising a valve 214B; and reservoir 210C via a tube 212C comprising a valve 214C. The valves 214A to 214C control the flow rates of the respective gases into the chamber.

The valves 214A to 214C are for example electronically controlled by a computing device 216. The computing device 216 for example comprises a processing device 218, under the control of an instruction memory 220 storing program code for controlling at least part of the graphene formation process.

The outlet 208 is for example coupled via a tube 222 to an evacuation pump 224 for evacuating gases from the reaction chamber 202. The rate of evacuation by the pump 224 is for example also controlled by the computing device 216. As represented by an arrow 226, the computing device may also control one or more heating elements of the reaction chamber 202 to heat the interior of the chamber during the graphene formation process.

A method of forming a graphene film using the apparatus described above is for example discussed in more detail in the US patent application published as US 2014/0326700, the contents of which are hereby incorporated by reference.

Furthermore, a deposition chamber 228 is for example provided for depositing the polymer layer over the graphene film. In the embodiment of FIG. 2, a trapdoor 230 in one wall of the chamber 202 and a passageway 231 between the chambers 202, 228 permits the substrate 204 with graphene film to be transferred between the chambers 202 and 228 without being exposed to the atmosphere. In alternative embodiments, the deposition chambers 202 and 228 could be separate from each other, and the substrate 204 with graphene film could be transferred without using a passageway.

Figure 3A:
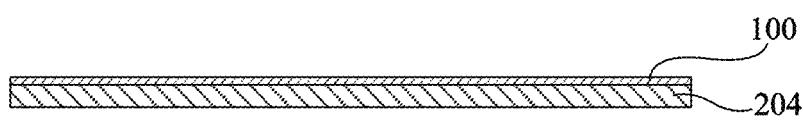
FIGS. 3A to 3C are cross-section views of the formation of a graphene device according to an embodiment of the present disclosure.
Figure 3B:
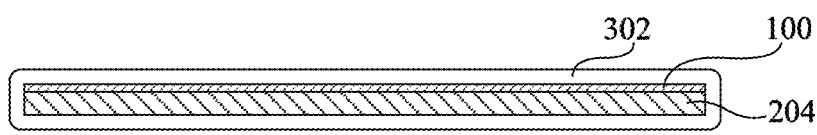
Figure 3C:
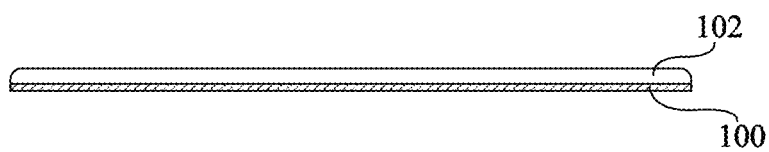

The deposition chamber 228 for example comprises an inlet 233 coupled via a further valve 214D to a supply chamber 234 for providing a precursor for depositing the polymer material to cover the graphene film. The valve is for example controlled by the coupling device 216. As mentioned above, the polymer material is for example deposited using gas phase deposition. The term "gas phase deposition" is considered here to include physical vapor deposition (PVD), chemical vapor deposition (CVD and atomic layer deposition (ALD). The precursor is for example heated in the supply chamber 234 to between 100° C. and 500° C. before being introduced as a vapor phase into the chamber 228 via the valve 214D. FIGS. 3A to 3C are cross-section views of a graphene device during its fabrication, for example using the apparatus of FIG. 2.

As shown in the FIG. 3A, initially it is assumed that a graphene film 100 has been formed by CVD over a substrate 204, which is for example a copper foil.

FIG. 3B illustrates an operation in which the polymer support is deposited covering the graphene film 100. In the example of FIG. 3B, the graphene is deposited over a relatively flat substrate 204, and the polymer material is deposited as a conformal layer 302 of substantially uniform thickness that encapsulates the device, including the substrate 204. For example, the device is turned over during the deposition process such that the polymer material is coated on all sides of the device. In alternative embodiments, the polymer material could be deposited only over the graphene film 100. Furthermore, rather than being deposited in the form of a layer, the polymer material could be deposited in other forms, as will be described in more detail below.

FIG. 3C illustrates a subsequent operation in which the substrate 204 is removed, for example by an etching step or by delaminating the graphene film 100 from the substrate 204. For example, the etching step involves removing the polymer coating covering the substrate 204, for example using a plasma etch, or by scraping with a sharp blade, in order to expose the surface of the substrate.

The substrate is then removed, for example using a suitable etch, such as an acid etch or using an electrolysis technique.

This leaves the graphene film 100 with the polymer support 102. The present inventors have found that the polymer support 102 advantageously reduces degradation of the graphene film 100 during the separation of the graphene film 100 from the substrate 204.

An advantage of the process described herein is that no transfer operation is required, reducing the risk that the properties of the graphene film will be degraded. Indeed, graphene is generally formed using a chemical vapor deposition (CVD) process, wherein graphene is deposited over a base substrate such as a copper foil. However, a difficulty is that it is relatively difficult to remove the graphene layer from the base substrate without damaging or polluting the graphene layer and/or degrading its conductivity.

By depositing a polymer material by gas phase deposition in contact with the graphene film, the polymer can remain attached to the graphene while the substrate is removed, for example by etching or by a delamination process, without a transfer step.

The process for forming a graphene device as described in relation to FIGS. 3A to 3C may be adapted to form a number of particular graphene-based medical devices as will now be described with reference to FIGS. 4 to 6.

Figure 4A:
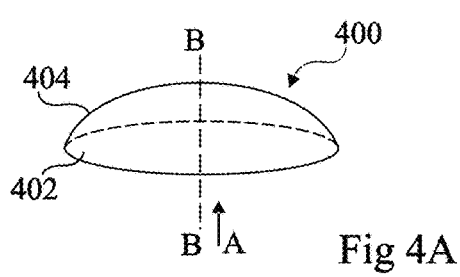
FIG. 4A illustrates an ophthalmic element comprising graphene according to an example embodiment of the present disclosure.
Figure 4B:
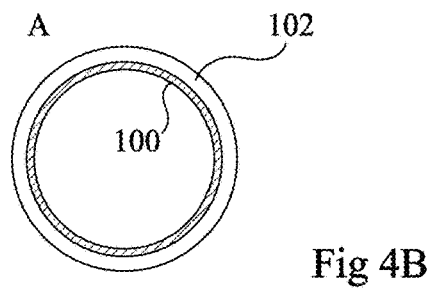
FIG. 4B is an underside view of the ophthalmic element of FIG. 4A according to an example embodiment.

FIG. 4A illustrates an ophthalmic element 400 comprising graphene that is adapted to be placed on the surface of the eye. The element 400 is for example in the form of a curved plate, the outer edge of which is circular in the example of FIGS. 4A to 4D, but could have a different shape. The element 400 for example has a concave underside 402 for contacting the surface of the eye, and a convex outer surface 404, having a form that permits an eyelid to close over the element 400. The element 400 for example has a diameter of between 8 and 20 mm. FIG. 4B is an underside view of the element 400 in a direction represented by an arrow A in FIG. 4 looking towards the concave side of the element. As illustrated, the element for example comprises a graphene film 100 and a polymer support layer 102. The graphene film 100 is for example exposed on the inside surface of the element 400, such that it can make electrical contact with the surface of an eye. The polymer layer 102 provides a support for the graphene film 100, and is formed in contact with the graphene film 100 and exposed on the outer surface of the element 400. The polymer material used for the support 102 is for example parylene, in view of the biocompatible nature of this polymer.

Figure 4C:
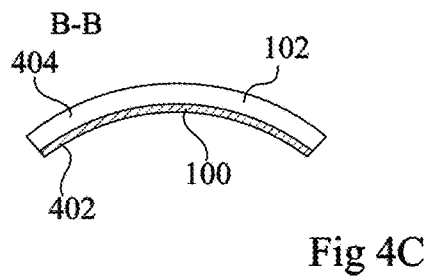
FIG. 4C is a cross-section view of the ophthalmic element of FIG. 4A according to an example embodiment.

FIG. 4C illustrates a cross-section B-B through the element of FIG. 4A, and as illustrated, the graphene film 100 and polymer support 102 together form a curved multi-layer.

Figure 4D:
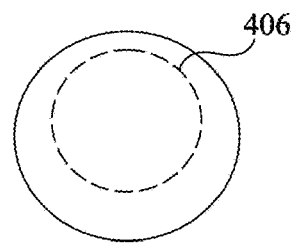
FIG. 4D illustrates a processing step for forming the ophthalmic element of FIG. 4A according to an example embodiment.

FIG. 4D represents a method step during the fabrication of the ophthalmic element 400 according to an example embodiment. The element is for example formed using a substantially spherical substrate, for example formed of a ball of copper, having at least approximately the dimensions of a human eye. The graphene film 100 is then for example formed by CVD on this substrate, and a polymer layer 102 is deposited by gas phase deposition over the graphene film 100. As represented by a dashed circle 406, a portion of the graphene/polymer multi-layer is then for example cut from the sphere in the shape of the ophthalmic element 400 and separated from the substrate, for example by a delamination process as described above, or by etching the copper forming the substrate.

Alternatively, an electrochemical delamination process may be performed as described in more detail in the publication entitled "Electrochemical delamination of CVD-Grown Graphene Film: Toward the Recyclable Use of Copper Catalyst", Yu Wang et al., the contents of which is hereby incorporated by reference to the extent permitted by the law.

While an example is illustrated in FIGS. 4A to 4D in which the graphene film 100 is continuous across the ophthalmic element, the graphene film 100 could be patterned. For example, the mold used to form the ophthalmic element could comprise two different materials, one of the materials supporting graphene growth and the other material not supporting graphene growth.

The patterning of these two materials across the surface of the mold on which the graphene is to be formed is selected based on the desired graphene pattern. An example of a material not supporting graphene growth is aluminum oxide. As an alternative example, a graphene etching step could be used to pattern the graphene film. The ophthalmic element 400 may have a variety of applications, including acting as an electrode on the surface of the eye. For example, the ophthalmic element 400 could form the eye-mountable device described in the patent publication US 2014/010744, in which layers of ITO (indium tin oxide) are replaced by the graphene film described herein. Alternatively, other applications of the ophthalmic element 400 include an ophthalmic shielding device, for example for shielding the eye from electromagnetic radiation such as microwaves.

Figure 5A:
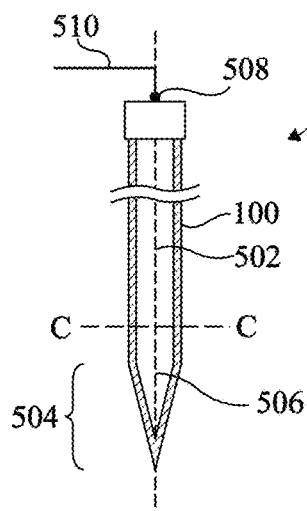
FIGS. 5A and 5B are a cross-section views of a medical implant comprising graphene according to an example embodiment of the present disclosure.

FIG. 5A is a cross-section view of a medical implant 500 comprising graphene. The element 500 is for example adapted to be inserted into human or animal tissue to act as an electrode. For example, in some applications the implant is used to monitor or stimulate neural activity. The implant is for example similar to the one disclosed in the US patent publication US2013/0090542, the contents of which is hereby incorporated by reference to the extent permitted by the law. However, whereas this document described an electrically conductive core material with an electrically non-conductive biocompatible polymer coating, the implant of FIG. 5A comprises a polymer core having an electrically conductive coating formed by a graphene film.

Indeed, as illustrated in FIG. 5A, the implant 500 for example comprises a polymer core 502 in the form of a needle, for example of parylene or polyimide, covered by a graphene film 100. The element 500 has a pointed end 504, which in the example of FIG. 5D has its point aligned with an axis 506 of the shaft of the needle, although in alternative embodiments the point coupled be offset with respect to this axis. The implant for example has a length of between a few millimeters and up to several tens of centimeters, depending on the application.

In some embodiments, some portions of the outer surface of the implant 500 could be formed of material other than graphene. For example, the point of the implant 500 could be formed of silicon or another material. The implant comprises, for example at an opposite end to the point 504, an electrode 508, which contacts the graphene film 100. The electrode 508 for example electrically couples the graphene film 100 to a wire 510, allowing electrical signals to be applied to the implant and/or electrical signals from the implant to be detected.

Figure 5B:
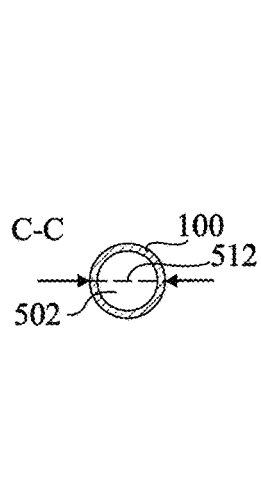

FIG. 5B is a cross-section view taken along a line C-C of FIG. 5A traversing a shaft of the implant between the pointed end 504 and the electrode 508. As shown, the implant is for example substantially circular in cross-section, although in alternative embodiment other shapes would be possible. A diameter of the implant is for example in the range 20 μm to 500 μm.

Figure 5C:
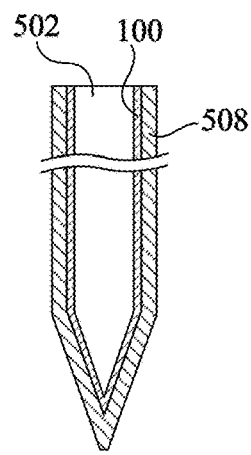
FIGS. 5C and 5D are cross-section views showing steps in a method of forming the implant of FIGS. 5A and 5B according to an example embodiment.
Figure 5D:
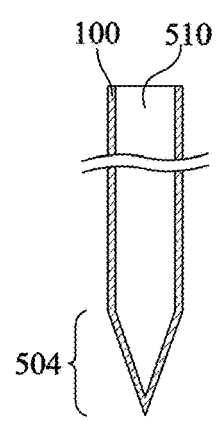

FIGS. 5C and 5D are cross-section views illustrating examples of process steps for forming the implant 500 of FIG. 5A.

As shown in FIG. 5C, the implant of FIG. 5A is for example formed using a mold 508, for example formed of copper, and having an inside surface having the desired outer form of the implant 500. The graphene film 100 is then for example formed by CVD on the inside surface of the mold, for example using the chamber 202 of the apparatus of FIG. 2. A gas phase deposition of the polymer support 502 is then performed to fill the mold 508, and contact the graphene film 100.

As shown in FIG. 5D, the mold 508 is then removed, for example using an etching step, leaving the shaft and pointed end 504 of the implant 500. The electrode 508 (not shown in FIG. 5D) is for example in the form of a cap placed over the end of the implant, opposite to the pointed end 504. Alternatively, the electrode 508 could be formed by a portion of the mold that is for example protected so that it is not etched when the rest of the mold is removed, and which thus remains in contact with the graphene film 100.

Figure 6A:
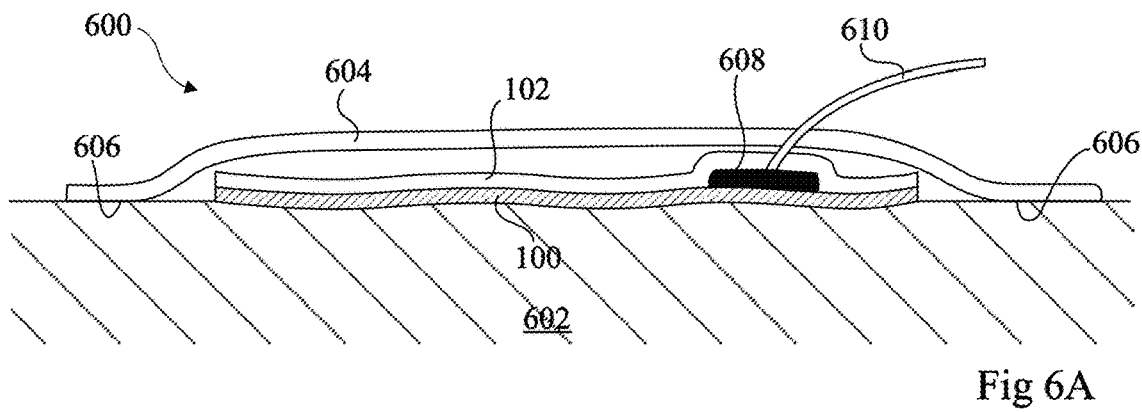
FIG. 6A is a cross-section view of a medical patch comprising a graphene film according to a further embodiment of the present disclosure.

FIG. 6A is a cross-section view of a conductive patch 600 comprising a graphene film 100. FIG. 6A illustrates an example in which the patch is employed contacting the surface of a portion of skin 602 of a human or animal body. The graphene film 100 of the patch is for example positioned to be exposed to and make contact directly with the surface of the skin 602, and it has a support 102 of polymer material in the form of a layer formed over it. The polymer layer 102 is for example of parylene. A further band 604 of polymer for example covers the graphene and polymer multi-layer 100, 102, and holds it in place against the skin. For this, the band 604 for example extends beyond the multi-layer 100, 102 on each side to make direct contact with the surface of the skin 602. It also for example has an adhesive layer 606 over at least a portion of its surface that contacts with the skin 602.

An electrode 608 for example contacts the graphene film. The polymer layer 102 for example has a thickness of between 10 nm and 5 mm, and an opening is formed in a portion of the polymer layer 102 in order to expose the surface of the graphene film. The electrode 608 is then for example formed on the graphene film, and in some embodiments, a further polymer deposition is performed to cover the electrode 608. An antenna 610 for example couples the electrode 608 to a monitoring device, passing through the band 604. In order to improve electrical contact with all parts of the graphene film 100, in a particular embodiment a device according to the invention comprises more than one electrode 608, wherein each of said electrode 608 is coupled to an antenna 610. In a more particular embodiment, a device according to the invention comprises two electrodes 608, wherein each of said two electrodes 608 is coupled to an antenna 610.

The patch 600 of FIG. 6A is only represented in cross-section, and it will be clear to those skilled on the art that in plan view the graphene/polymer multi-layer 100, 102, and the band 604, could have any form, for example rectangular or circular.

The graphene film 100 for example has a surface area of between 5 and 50 mm$^2$ that contacts the skin 602.

An advantage of the embodiment of FIG. 6A is that the graphene/polymer multi-layer 100, 102 is relatively supple, enabling it to follow contours in the surface of the skin, including wrinkles, while maintaining relatively high conductivity with the skin 602.

In the example of FIG. 6A, the electrode 608 contacts a relatively small zone of the graphene film 100. However, in order to improve electrical contact with all parts of the graphene film 100, in alternative embodiments the electrode 608 is substantially annular, making contact in a perimeter zone of the graphene film 100, as will now be described with reference to FIG. 6B.

FIG. 6B is a plan view of the graphene film 100, and also illustrates an annular electrode 608 used for making electrical contact with the graphene film 100. In particular, the electrode 608 for example surrounds the zone in which the graphene film 100 makes contact with the wound. For example, the electrode 608 is formed of a material such as a resin or glue mixed with carbon to render it conductive. While an example is illustrated in which the electrode 608 is annular, other forms would be possible, such as rectangular.

In some applications, the patch 600 could be used for administering a medicine and/or for the treatment of open wounds, as will now be described in more detail with reference to FIGS. 7A, 7B and 8.

FIG. 7A illustrates an apparatus 700 for treating wounds and/or administering medicine using the medical patch 600 of FIG. 6A. As illustrated, the patch 600 is for example applied as a wound dressing covering an open wound 701.

Alternatively, the patch 600 could be applied to skin in a similar fashion to the example of FIG. 6A, and used for drug delivery. A further patch 702, which is for example very similar to the patch 600, is for example applied to the patient's skin in the vicinity of the wound, for example within a distance of 20 cm or so from the wound. The features of the patch 702 have been labelled with like reference numerals to the patch 600, and will not be described again in detail. In alternative embodiments, a different type of conductive patch could be used to implement the further patch 702.

The electrodes 608 of each of the patches 600, 702 are for example coupled to a voltage application module 710. The module 710 is for example adapted to apply voltage pulses across the electrodes 608 of the patches 600, 702 in order to drive a current through the patient's tissue in the vicinity of the wound 701 or the patient's skin. Medicine is for example delivered through the skin by the patch 600 using a process of iontophoresis. In such a case, the medicine is for example in the form of a cream or gel positioned between the graphene film 100 and the skin. A DC current of between 0.1 and 5 mA is for example applied between the electrodes of the patches 600, 700. For example, thus us achieved by applying a voltage in the range 5 to 40 V. This for example generates a current density in the skin of between 0.01 and 0.1 mA/cm$^2$. In some embodiments, a pulsed signal rather than a DC signal could be applied.

For wound treatment, a process of electrical stimulation is for example performed, as described in more detail in the publication by L. C. Kloth entitled "Electrical Stimulation Technologies for Wound Healing", Adv Wound Care, Feb. 1, 2014, 3(2): 81-90, the contents of which is hereby incorporated by reference. For such a treatment, there are various possible voltage levels and frequencies that could be employed. In some embodiments, a DC signal could be applied, for example having a voltage in the range of 5 to 60 V. Alternatively, a monophasic or diphasic pulsed current could be applied, having a frequency of anywhere between 1 and 100 kHz, and a voltage for example in the range 50 to 500 V.

FIG. 7B illustrates a medical patch 750 for treating wounds and/or administering medicine similar to that of FIG. 7A, but in which both the wound dressing portion 600 and the electrode patch 702 use the annular electrode 608 of FIG. 6B.

FIG. 7C illustrates a view of the medical patch 750 taken in a plane A-A shown in FIG. 7B passing through the annular electrodes 608 of the wound dressing 600 and of the electrode patch 702.

The medical patch 750 of FIGS. 7B and 7C comprises both the wound dressing portion 600 covering a wound 701, and the electrode patch 702 contacting the patient's skin, under a same adhesive band 752 that holds the wound dressing 600 and electrode patch 702 in electrical contact with the patient. Furthermore, in the example of FIGS. 7B and 7C there is no wire leaving the patch 750, and instead the patch 750 comprises a circuit 754 coupled by wires to the annular electrodes 608 of the wound dressing 600 and electrode patch 702. The circuit 754 for example comprises a power source, such as a battery, for driving a current between the graphene films 100 of the wound dressing 600 and electrode patch 702. In other embodiments, in addition to or instead of using a battery, the circuit 754 may comprise a coil antenna and a capacitor fed with charge generated by the coil antenna. In this way, the wound dressing can be powered wirelessly using a non-contact inductive coupling. For example, such a wireless non-contact inductive coupling is described in more detail in the US patent application published as US20140336597, the contents of which are hereby incorporated by reference to the extent permitted by the law.

FIG. 8 illustrates an example of the voltage signal applied to across the electrodes 608 of the patches 600, 702 to provide electrical stimulation for wound healing. For example, the voltage pulses have a peak voltage amplitude Vp of around 100 V. Each pulse for example has a duration $t_{pulse}$ and the no-current interval between successive pulses represents up to 99% or more of each period $t_{period}$ such that the total current per second delivered to tissue does not exceed more than 1.2-1.5 mA. Thus for a voltage Vp of 100 V, the paired pulse charge is for example only around 3-3.5 µC, and for a pulse rate of 100 pulses/s, the total charge accumulation (dosage) does not for example exceed 350 µC/s.

Such a treatment is for example applied for a period of between 5 and 60 minutes, and repeated on a daily basis until the wound has healed.

In some embodiments, the apparatus 700 of FIG. 7A or medical patch 750 of FIG. 7B further comprises means for detecting the resistance of the wound between the graphene film 100 of the wound dressing 600 and the graphene film 100 of the electrode patch 702. For example, the voltage application module 710 of FIG. 7A and/or the circuit 754 of FIG. 7B comprises a current sensor and/or voltage sensor for detecting the current and/or voltage applied between the wound dressing 600 and the electrode patch 702, enabling the resistance to be determined. For example, the measured resistance may provide an indication of the state of the wound, a high resistance indicating that the wound is becoming dry and/or is healing.

In some embodiments the graphene film 100 of the wound dressing 600 could also be patterned to form a plurality of pixels such that the resistance information of the pixels can provide an image of the wound. For example, the graphene film could be pattered as shown in FIG. 7 of the U.S. Pat. No. 7,945,302, and the teaching described in this document could be applied to the medical patch described herein to provide such an image. The contents of U.S. Pat. No. 7,945,302 is hereby incorporated by reference to the extent permitted by the law.

Advantageously, at least part of the graphene film 100 of the patch 600 remains in place on the tissue of the patient when the patch is removed, as will now be described with reference to FIG. 9.

Figure 9:
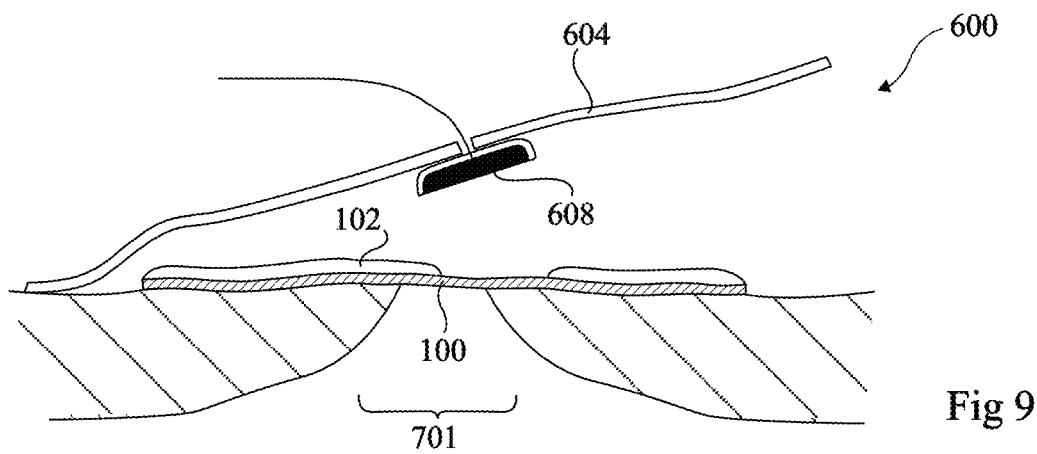
FIG. 9 illustrates removal of the patch of FIGS. 6 and 7 according to an example embodiment.

FIG. 9 illustrates the patch 600 in the process of being removed, for example after the wound 701 has started to heal and has thus reduced in size. The band 604 and the electrode 608 of the patch 600 for example separate from the multi-layer of graphene 100 and polymer 102, which remain covering the wound 701.

For example, an adhesive is present between the protrusion formed by the electrode 608 and the band 604, such that the electrode is pulled away as the band 604 is removed from the skin. However, there is for example no adhesive, or a relatively weak adhesive, present between the graphene/polymer multi-layer and the band 604. Advantageously, graphene is a material that will be progressively absorbed by tissue. Furthermore, a polymer layer that is relatively thin, for example formed of parylene of between 10 and 20 nm in thickness, can also be absorbed.

Alternatively, the graphene layer 100 may be a multilayer, and the polymer layer 102 may be glued or otherwise fixed to the band 604, such that the patch delaminates within the graphene layer 100. Thus only one or a few graphene layers for example remain covering the wound when the patch 600 is removed.

The advantage of leaving at least part of the graphene/polymer multi-layer covering the wound when the patch 600 is removed is that this reduces damage to wound caused by the removal process, and further reduces the chance of infection by leaving a barrier in place. Furthermore, it has been found that a graphene film can be absorbed by a body, meaning that the graphene film will be broken down and disappear without further intervention.

In some embodiments, only all or part of the graphene film 100 remains covering the wound, and the polymer film 102 remains attached to the band 604 when the wound dressing is removed. For example, the graphene film is formed of multiple layers of graphene, such that at least one layer of graphene remains attached to the polymer layer when the dressing is removed, and at least one layer of graphene remains covering the wound. In yet further embodiments, the polymer film 102 is formed of a material that can be absorbed by the body like the graphene film, so that even when the polymer layer remains covering the wound, it is broken down and removed naturally by the body. An example of such a polymer material that could be used to form the polymer layer 102 is hyaluronic acid.

Figure 10:
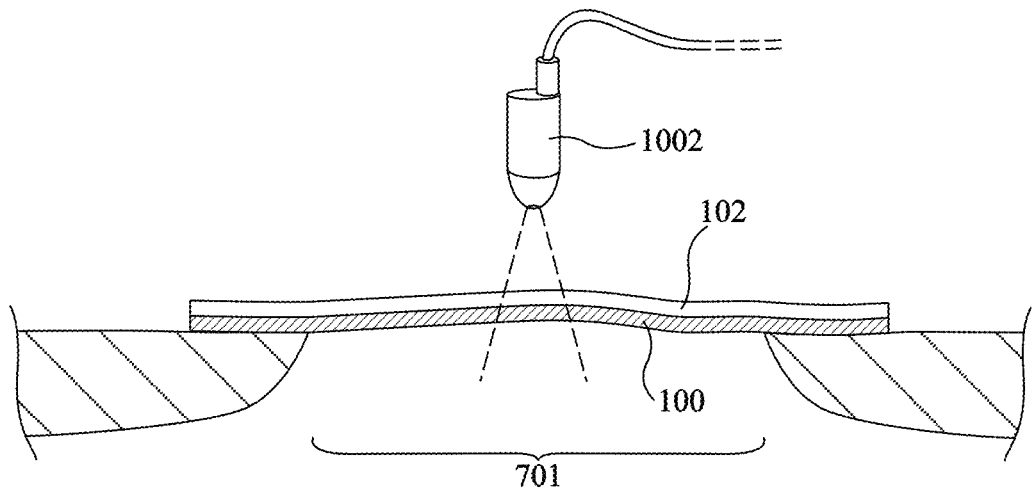
FIG. 10 is a cross-section view of a transparent wound dressing according to an example embodiment.

A further advantage of the use of a graphene and polymer structure for wound dressing is that the patch can be highly transparent. This is not only good for the aesthetics of the dressing, but also for example permits natural light to reach the wound, aiding the healing process. Furthermore, the transparency of the dressing permits the state of the wound during the healing process to be monitored visually and/or using specialized equipment. Indeed, graphene is grey in color and thus does not modify the color of the underlying wound, allowing this to be monitored visually. Furthermore, an analysis based on the Doppler Effect can be performed, known as LDF (Laser Doppler Flowmetry) as will now be described with reference to FIG. 10. FIG. 10 illustrates a wound 701 covered by a graphene/polymer patch 100, 102. A hand-held continuous wave Doppler laser equipment 1002 is used to take measurements of the wound for assessment. For example, the equipment 1002 is used for laser Doppler imaging as described in more detail in the publication by Stan Monstrey et al. entitled "Assessment of burn depth and burn wound healing potential", BURNS 34 (2008) 761-769, and/or in the publication by G. C. Zografos et al. entitled "Laser Doppler Flowmetry in Evaluation of Cutaneous Wound Blood Flow Using Various Suturing Techniques", LASER DOPPLER FLOWMETRY, Vol. 215, No. 3, Ann. Surg. March 1992, the contents of these publications being incorporated herein by reference to the extent permitted by the law. For example, analysis may be based on a detection of the speed of red blood cells in the wound, where movement of the red blood cells above a certain speed indicates a healthy healing process, and slow moving or stationary red blood cells indicates an unhealthy wound.

While FIG. 10 illustrates a case in which the adhesive band 604 is removed prior to performing LDF, in alternative embodiments, the adhesive band 604 could be transparent, permitting LDF to be performed without removing the adhesive band 604.

Figure 11:
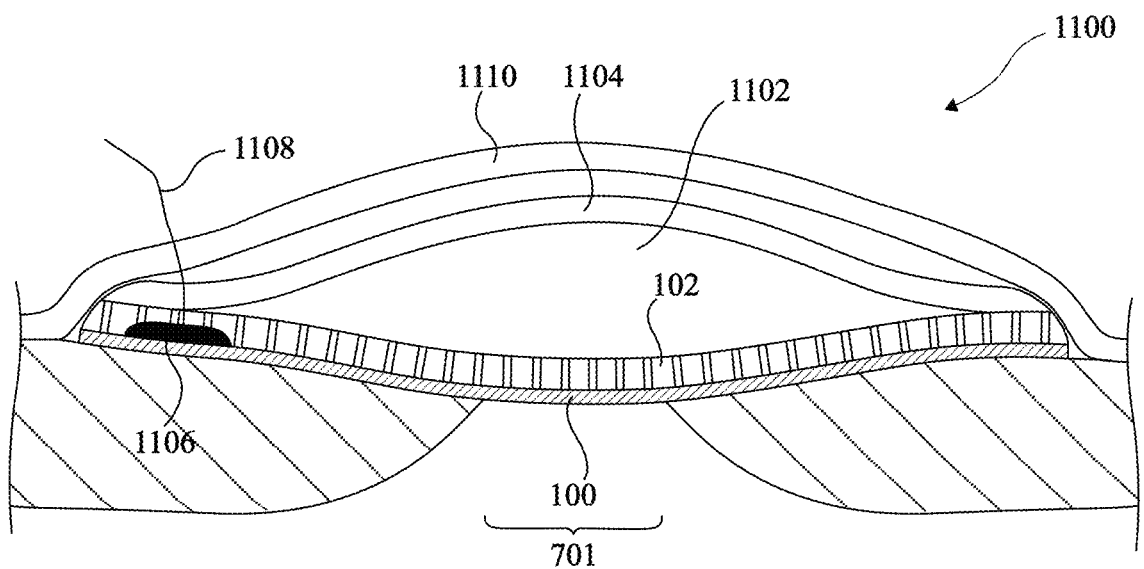
FIG. 11 is a cross-section view of a hydrocolloidal dressing according to an example embodiment.
Figure 12A:
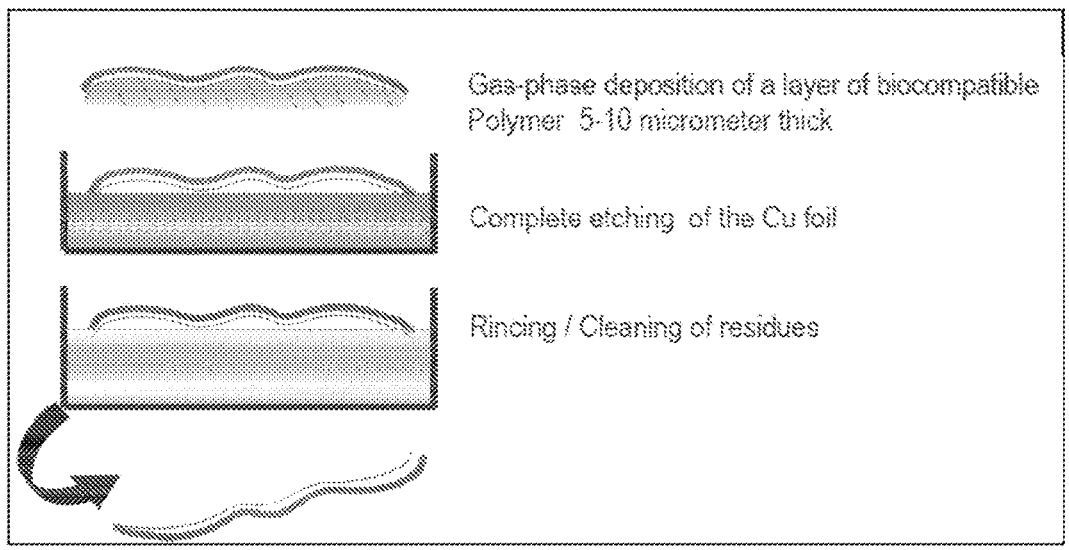
FIGS. 12A and 12B, schematically represent a process according to the invention (FIG. 12A) and a process of prior art (FIG. 12B)
Figure 12B:
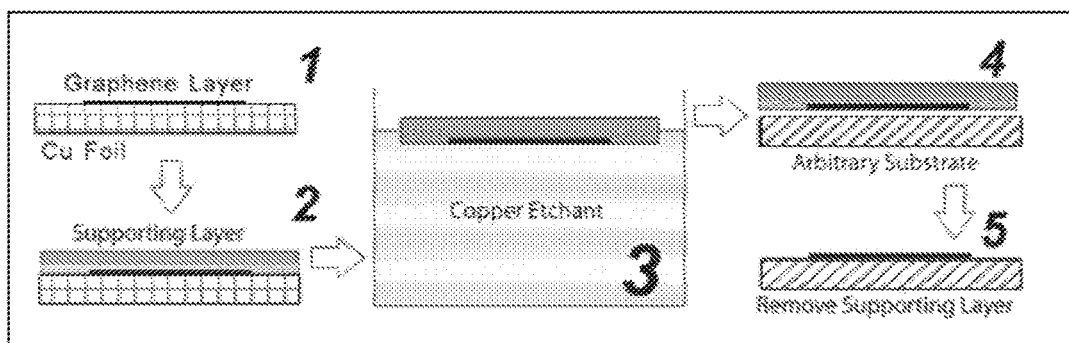
Figure 13:
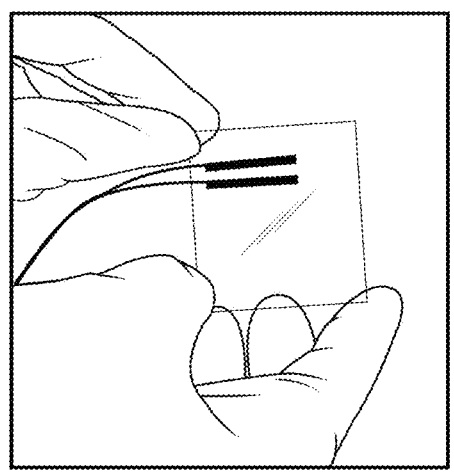
FIG. 13 is an illustrative picture of a device according to the invention.

FIG. 11 is a cross-section view of a conductive patch 1100 comprising a graphene film 100. FIG. 11 illustrates an example in which the patch provides a hydrocolloidal blister dressing. This dressing for example comprises a porous polymer layer 102. For example, the polymer material could be hyaluronic acid, which is inherently porous, or the polymer material could be parylene or another non-porous polymer which is rendered porous by creating channels through the layer for example using a lithography step, thereby providing a micro-structure.

The channels through the porous polymer layer 102 permit oxygen and water to flow between the wound and a pad 1102 formed of a hydrocolloid. The pad 1102 is for example held by a layer 1104 of a non-porous polymer material. The hydrocolloid acts as a sponge, absorbing the exudate from the wound, and providing moisture to the wound if it becomes dry. The graphene film 100 contacts the wound or blister, and is electrically coupled, for example via a contact 1106, with a wire 1108. An adhesive band 1110 is for example provided for holding the hydrocolloidal dressing in contact with the wound.

In operation, the graphene film 100 can receive an electrical current as described in relation to FIGS. 7A and 7B using a further electrode patch (not illustrated in FIG. 11).

Furthermore, Laser Doppler Flowmetry (LDF) as described above in relation to FIG. 10 could also be performed in the embodiment of FIG. 11, the pad 1102 and some or all of the layers 100, 102, 1104 and 1110 for example being transparent such that LDF can be performed through them.

An advantage of the devices, and preferably of the medical devices, described herein is that they have a good electrical conductivity due to the graphene film, and are capable of maintaining close electrical contact with the skin or tissue of the human or animal due to the use of the polymer material supporting the graphene film which adapts to contours in the surface of the body against which the device is applied.

Furthermore, by using a graphene formation process in which a polymer layer is deposited over the graphene film using gas phase deposition, the electrical conducting properties and mechanical properties of the graphene film can be particularly well conserved as the mold is removed. Indeed, gas phase deposition allows a thin polymer coating of relatively uniform thickness to be applied that has high conformity with the roughness of the surface of the graphene film, by closely following the contours of the graphene film. In view of its high conformity and uniformity, such a polymer layer exerts a lower stress on the graphene layer than would be possible with other deposition techniques such as spin coating.

Furthermore, gas phase deposition allows a supporting polymer layer to be realized that strictly conforms to a 3-dimensional shape of the graphene film, both at the nanoscale and at the microscale, respectively helping to preserve the integrity of the film by matching the wrinkles and thereby providing good electrical conductivity and helping to maintain the global 3D shape of the graphene film after the mold removal, allowing depositions on complex shapes such as implants, etc.

Having thus described at least one illustrative embodiment, various alterations, modifications and improvements will readily occur to those skilled in the art.

For example, it will be apparent to those skilled in the art that while various devices comprising graphene have been described above and represented in the figures, there are many alternative applications of the method of forming the graphene and polymer multi-layer as described herein.

Furthermore, the various features described in relation to the various embodiments could be combined, in alterative embodiments, in any combination.

For example, the use of hyaluronic acid to form the polymer layer and provide a therapeutic action may be combined with the use of a pad of a hydrocolloid positioned close to the wound to absorb exudate from the wound.

A device comprising a graphene film of the present invention is capable of sensing local change of static charges in the direct vicinity of graphene in particular those coming from biochemical reactions or change of acidity in the liquid medium in contact.

The present invention further relates to a method for monitoring wound healing using a device according to the invention. Said method for monitoring wound healing comprises, first, contacting the body of an individual, human or animal, in the location of a wound, with a device according to the invention, wherein said device is connected to a measurement apparatus, in particular a current sensor and/or a voltage sensor, either via wire or antenna connection and, second, measuring electrical parameters of the graphene film of a device according to the invention. A method of monitoring wound healing according to the invention involves measuring in time, said electrical parameter, such as resistance. Said measure is possibly a continuous or a discontinuous measure in time. An illustration of said method is given in Example 4.

The present invention further relates to a method for stimulating wound healing using a device according to the invention. Said method for stimulating wound healing comprises, first, contacting the body of an individual, human or animal, in the location of a wound, with a device according to the invention, wherein said device is connected to a pulse generator, either via wire or antenna connection and, second, measuring electrical parameters of the graphene film of a device according to the invention. A method of stimulating wound healing according to the invention involves measuring in time said electrical parameter, such as resistance. An illustration of said method is given in Example 4. According to this embodiment, a device comprising a graphene film, according to the invention, is placed on a wound and connected from its side via carbon electrodes. The two electrodes are connected to a pulse generator capable of sourcing a single pulse or a train of pulses of typically 0.1 ms separated by 0.1 ms, with for example a repetition time of 100 Hz. The intensity of the pulse is from 200 micro ampere up to 1 mA.

Such alterations, modifications, and improvements are intended to be within the scope of the invention. Accordingly, the foregoing description is by way of example only and is not intended as limiting. The invention is limited only as defined in the following claims and the equivalents thereto.

EXAMPLES

Figures 14A, 14B:
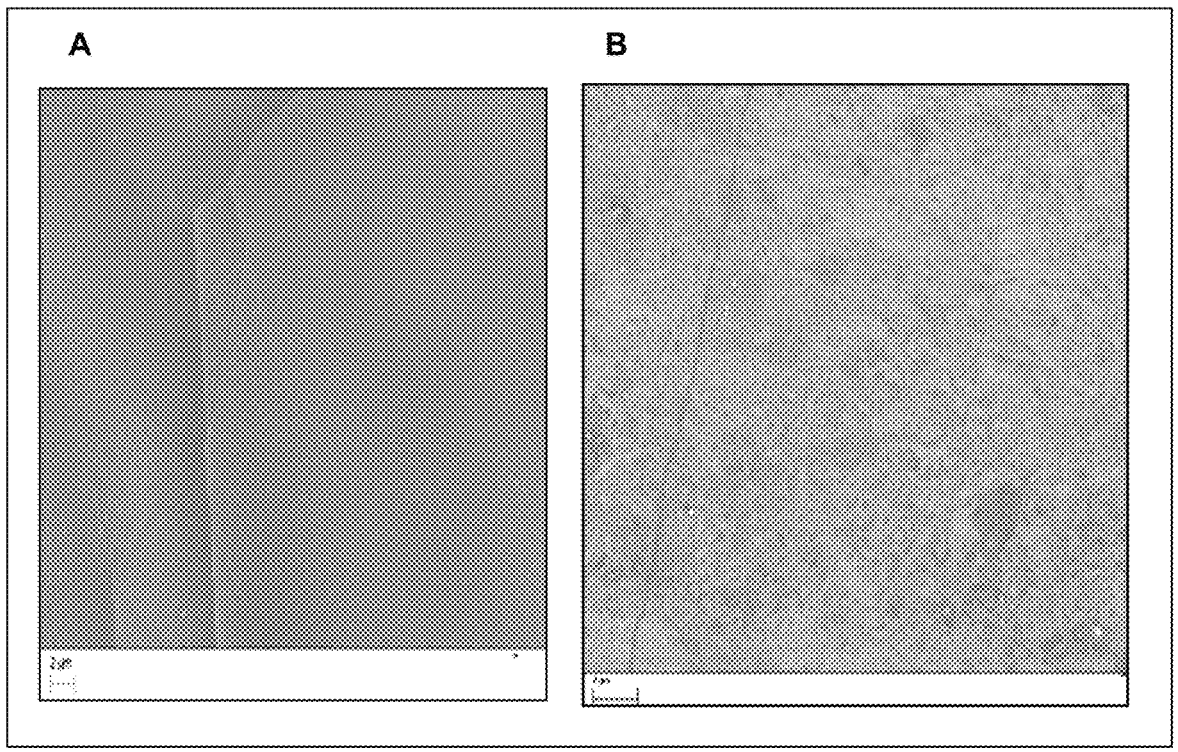
FIGS. 14A and 14B, in example 1, represent the scanning electron microscope comparison, side by side, on same area, of a graphene film in a device according to the invention (FIG. 14A) and of a graphene film in a device according to prior art (FIG. 14B), FIGS. 15A and 15B, in example 1, represent the atomic force microscope comparison, side by side, on same area, of a graphene film in a device according to the invention (FIG. 15A) and of a graphene film in a device according to prior art (FIG. 15B), FIG. 16, in example 2, represents the statistical dispersion of surface resistivity of graphene-on polymer (expressed in units of kilo-Ohms per square) of samples of monolayer graphene transferred on polymer sheets; graphene on parylene samples prepared using the method disclosed in the present invention (hatched dark grey histograms) are compared to samples of same geometry transferred on Polyethylene terephthalate (PET) substrate using PMMA liquid transfer method according to prior art (grey histograms).
Figures 15A, 15B:
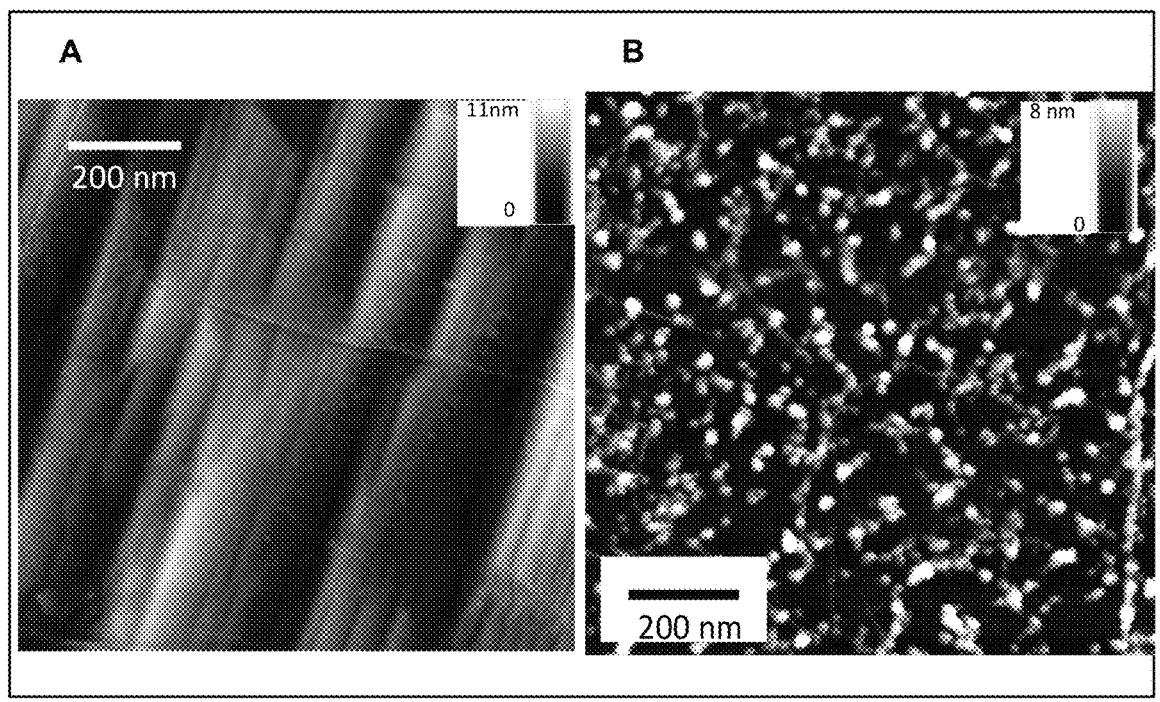

Example 1: Microscopic Comparison of Devices Comprising Graphene According to the Invention and According to Prior Art Surface contamination states are assessed using two types of microscopies: Scanning electron microscopy (SEM, FIGS. 14A & B) and Topographic atomic Force Microscopy (AFM, FIGS. 15A & B). While a process according to the invention give rise to more wrinkled surface compared to prior art due to the peculiar nature of the process, the contrast of the images confirms the polymeric nature of the residues (FIG. 14B) and their high density and significant roughness (FIG. 15B) are typical to those found on the surface of the graphene layer of devices of prior art.

Example 2: Comparison of Electronic Performance of Devices Comprising Graphene According to the Invention and According to Prior Art For benchmarking purposes, the electronic properties of graphene-on-parylene samples prepared using the method disclosed in the present invention are compared to those of samples of same geometry transferred on Poly Ether Phthalate (PET) films using the so-called PMMA liquid transfer method, as described in Picaud et al. (US 2015/0343202)

and in Hébert, C. et al. Flexible Graphene Solution-Gated Field-Effect Transistors: Efficient Transducers for Micro-Electrocorticography. *Adv. Funct. Mater.* (2017). doi: 10.1002/adfm.201703976}.

For sake of comparison, from a single batch of graphene on Copper sheet produced by the same CVD process, depositions of polymer films are performed as described in the respective process:
- gaseous CVD deposition of parylene film, according to the process of the invention, or
- liquid phase deposition of PMMA, according to the process of US 2015/0343202.

Copper is removed by the same technique of etching using Ammonium Persulfate solution. The PMMA samples are then transferred onto 75 micron-thick Polyethylene terephthalate (PET) films. The samples were then cut into rectangles of 0.5×1.5 cm and glued on a solid surface. Resistivity is measured using the a micro four-point probe method as described in Buron, J. D. et al.: "Electrically continuous graphene from single crystal copper verified by terahertz conductance spectroscopy and micro four-point probe". Nano Lett. 14, 6348-6355. https://doi.org/10.1021/nl5028167 (2014) and "Graphene conductance uniformity mapping. Nano Lett. 12, 5074. https://doi.org/10.1021/nl301551a (2012).

Both sets of data are measured on graphene originating from the same synthesis batch of monolayer CVD graphene and are transferred the same day.

Results are shown in FIG. 14 wherein graphene on parylene samples prepared using the method disclosed in the present invention (hatched dark grey) are compared to samples of same geometry transferred on Polyethylene terephthalate (PET) substrate using PMMA liquid transfer method.

The average electrical surface resistivity of graphene-on-parylene films is consistently reduced by 50% compared to prior art (PMMA wet transfer on PET films) on graphene-on-polymer. Furthermore, the statistical dispersion is also reduced by roughly 50%, indicating that the electronic properties of the graphene-on-parylene are improved both in quality and in reproducibility compared to state of the art.

Example 3: Study on a Large Hand-Made Graphene on Parylene Solution-Gated Field Effect Transistor (SGFET) According to the Invention In the present example, a device according to the invention is prepared as follows Single layer graphene was prepared by chemical vapor deposition (CVD). After an annealing of the copper foil at 1000° C. under hydrogen flow (35 sccm) for 15 min, the gas composition was changed to a hydrogen/methane mixture (10 sccm/35 sccm) and the graphene was let grown on copper foil at 1000° C. for 30 min. The resulting graphene on copper is then covered by a parylene C film using the standard deposition method. During the deposition, parylene C is initially vaporized from its solid dimer phase inside the vaporizer furnace at ~120° C. Next, the pyrolysis occurs in a high-temperature furnace (>600° C.), which converts the dimers to monomers by breaking the methylene-methylene bonds. In the last stage, the polymerization of the monomer takes place at room temperature on the substrate surface inside the deposition chamber at the pressure of ~0.1 mbar. The dimer quantity in weighted in order to reach a deposition thickness of 10 micrometers. In order to etch the copper substrate, the resulting stack is placed in a FeCl3 solution (0.5M) during 15 minutes. Afterwards, the graphene/polymer film was rinsed in pure deionized water and dried with Nitrogen.

A device according to prior art is prepared as follows: from a single batch of graphene on Copper sheet produced by the same CVD process as for the invention.

For the wet transfer of graphene to PET film, the copper/graphene films were covered by spin coating a solution poly(methyl 2-methylpropenoate) (PMMA) layer dissolved in dicholobenzene. The film is dried on a hot plate at 180° Celsius. This stack was placed on a FeCl3 solution (0.5M) in order to etch the copper substrate.

Afterwards, the graphene/polymer film was rinsed in pure deionized water and transferred onto PET film after which the PMMA was removed with acetone. The PMMA samples are then transferred onto 75 micron-thick Poly Ether Phtalate (PET) films. The sample were then cut into rectangles of 0.5×1.5 cm and glued on a solid surface. Resistivity is measured using the a micro four-point probe method. For the Field effect measurements, the graphene on polymer was cut and placed on a glass substrate. Two connections to contact the graphene sheet were made using silver paste. The contacts were insulated using an epoxy. An epoxy well is also formed to expose the graphene channel to a liquid solution.

The transfer curve measurement of the graphene SGFET was performed in Phosphate Buffered Saline (0.1M). A DAQ card NI6363 was used to supply voltage at the terminal of the transistor and to read the current. A current to voltage converter FEMTO DHCPA was used to measure the drain source current flowing through the transistor (Ids) and to convert it to a readable voltage for the DAQ card. The gate-source voltage (Vgs) was applied using an Ag/AgCl electrode. The applied drain source voltage was set to 100 mV. The width to length ratio of the transistor is difficult to determine due to the crude fabrication process.

No cleaning and optimisation process were performed and the device were measured as made after the epoxy step. The devices were not fabricated in clean room.

Figures 17A, 17B:
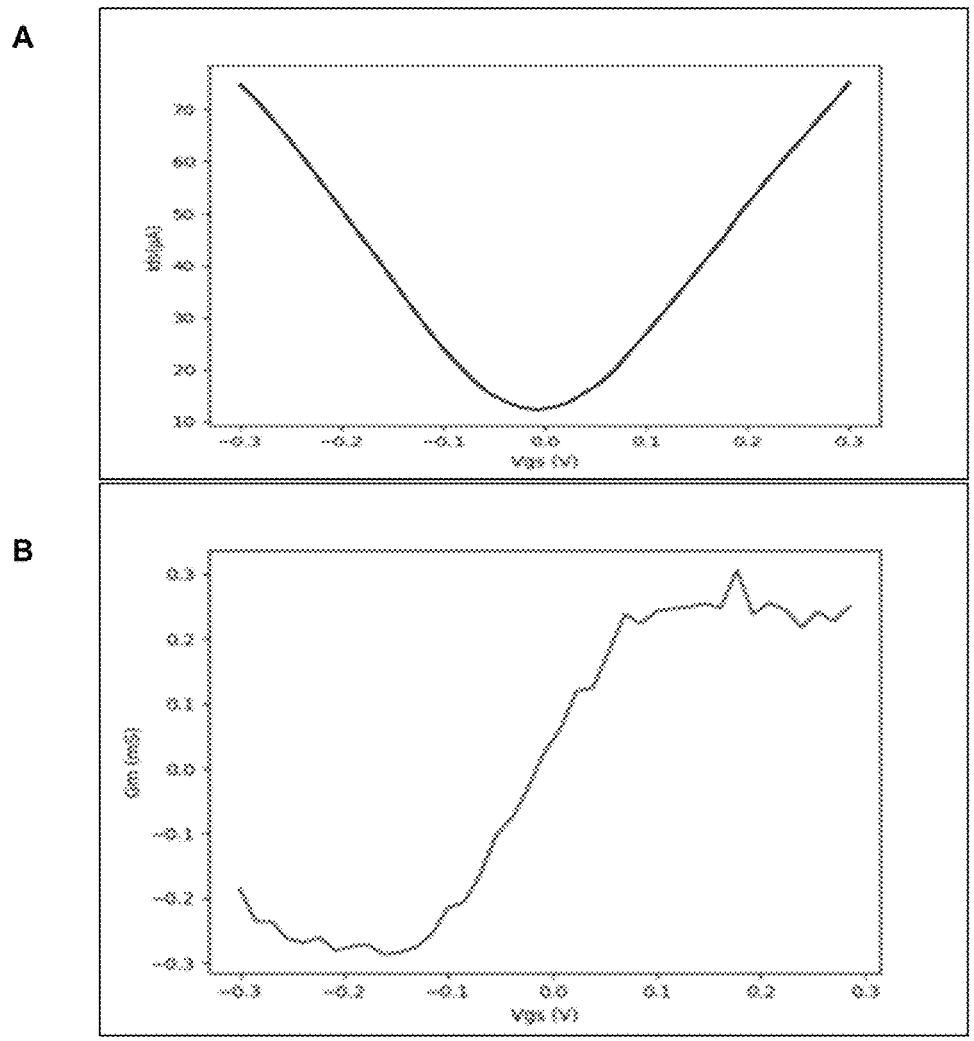
FIGS. 17a and 17b, in example 3, show respectively the transistor transfer curve representing the current flowing in a graphene device according to the invention as a function of gate voltage (FIG. 17aA) and the transconductance of a graphene device according to the invention as a function of gate voltage (FIG. 17b)
Figures 18A, 18B:
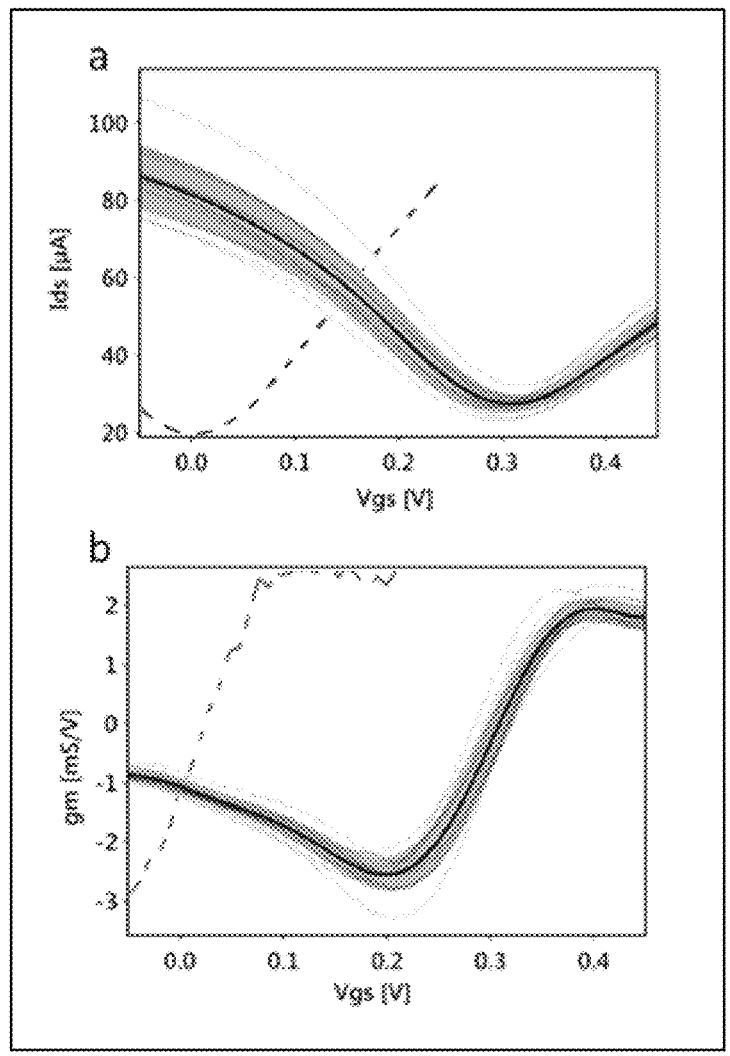
FIGS. 18A and 18B, in example 3, show a comparative illustration of the transistor transfer curve representing the current flowing in a graphene device according to the invention (hatched curve) and of a graphene device of prior art (continuous curve) as a function of gate voltage (FIG. 18A); wherein the transconductance of a graphene device according to the invention (hatched curve) and of a graphene device of prior art (continuous curve) as a function of gate voltage is shown in FIG. 18B.

Results are shown in FIGS. 17A, 17B and 18, which show that, from the first measurement (FIG. 17A), the transfer curve exhibits a charge neutrality point very close to 0 V. This indicates a very low doping level. The doping level strongly depend on the impurity density present at the graphene surface. So it can be concluded the impurity density at the graphene on parylene produced by the invention is very low.

Impurity density at the graphene surface is a major issue for its electronic properties. The high density of polymer residual at the graphene surface in the case of the prior art standard PMMA transfer process is one of the main reason why graphene electronics is not mature enough to compete with silicon-based technologies.

Figure 16:
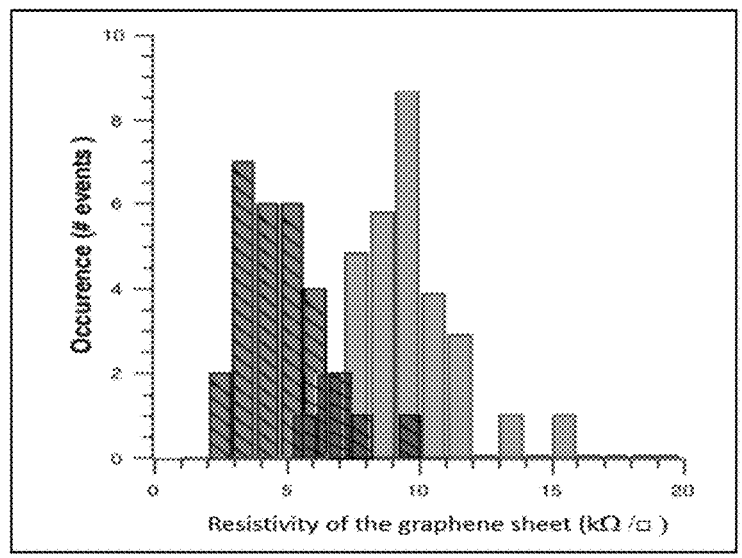

With devices according to prior art, even after careful annealing and cleaning process, the position of the charge neutrality point is always observed around 0.2 to 0.4 mV showing that the clear presence of polymer residuals (FIGS. 16a and 16b).

Several ways are used to remove those residuals. Among them High temperature under high vacuum annealing and chemical cleaning using toxic compound such as THF. Those two technics are very expensive and high temperature annealing cannot be used when dealing with polymers. Concerning the field effect mobility that could be roughly extracted from the transconductance curve it is between 800 and 1200 $cm^2$ $(V·s)-1$. These values are in the range or above the values obtained for a quasi-optimised transistor fabricated in a clean room environment. An accurate value cannot be determined due to the crude fabrication process that leads to high uncertainties on the length and width of the transistors as well as the lack of information on the contact resistance.

As a conclusion, the SGFET produced with the graphene of the invention shows very few impurities compare to PMMA transfer process. This is a great advantage for biomedical application of graphene where harsh treatment cannot be applied because of the polymer substrate. Finally, it is worth noticing that the better performances of graphene on parylene of the invention as SGFET compare to PMMA-based transfer technology of prior art were obtained on very crude, and not optimised nor cleaned devices.

Example 4: Characterization of a Device Comprising Graphene According to the Invention, Comprising 2 Electrodes As shown in FIGS. 19A and 19B, the two electrodes (608) are electrically contacting both sides of graphene film (100) and are electrically insulated from the environment top polymer layer (102) and by the back polymer passivation (103)

Figure 19A:
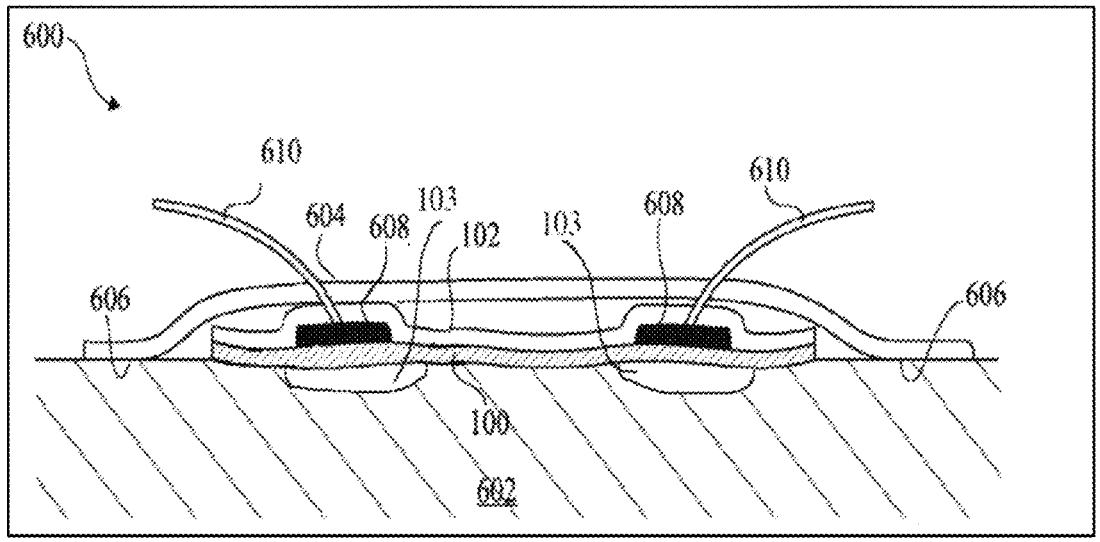
FIGS. 19A and 19B, in example 4, represent a cross-section view of a medical patch comprising a graphene film according to a further embodiment of the present disclosure wherein said graphene film bears two electrodes 608, said device may further comprise a polymer passivation layer 103 to isolate the electrode from the skin and therefore avoid direct contact of the skin and the metal, and may also comprise an impedance measurement device 711.
Figure 19B:
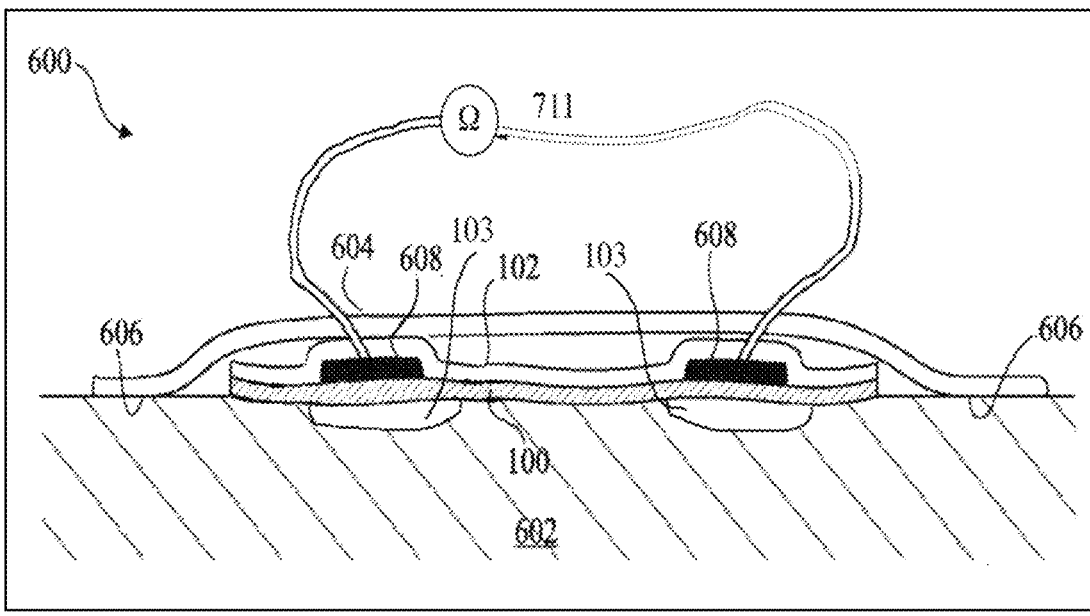

In FIG. 19A the electrodes are wired to an antenna while in FIG. 19B the two electrodes are connected to a measurement apparatus 711 capable of measuring the variation of resistance of the graphene film in contact with a fluid such as the exudates of a wound). The recording of this resistance in time gives important information about the wound healing process such as the evolution of the acidity of the wound, that is rapidly changing if the wound get infected.

In another embodiment, a graphene device according to the invention is placed on a wound and connected from its side via carbon electrodes. The two electrodes are connected to a pulse generator capable of sourcing a single pulse or a train of pulses of 0.1 ms separated of 0.1 ms with a repetition time of 100 Hz. The intensity of the pulse is between 200 micro ampere (A) up to 1 mA.

The invention claimed is:

1. A conductive device comprising a graphene film and a layer of polymer material covering a surface of the graphene film, wherein the polymer material forms a support for the graphene film; and wherein said device is characterized by a density of particulate contamination inferior to one contaminant per 10 square micron area of an exposed surface of said graphene film.

2. The conductive device of claim 1, wherein a charge neutrality point of the graphene film is inferior to 0.2V.

3. The conductive device of claim 1, wherein an electronic mobility of the graphene film is superior to 800 $cm^2(V \cdot s)^{-1}$.

4. The conductive device of claim 1, wherein a resistivity, for a sample of 1 $cm^2$, of the graphene film is characterized by a square resistance inferior to 10 kilo Ohm/square, preferably inferior to 7 kilo Ohm, more preferably comprised between 0.5 and 5 kilo Ohms/square.

5. The conductive device of claim 1, further comprising at least one electrode electrically coupled to the graphene film, said at least one electrode being optionally electrically coupled to a wire contact.

6. The conductive device of claim 1, wherein a thickness of the graphene film is from one atom to 8 atom layers.

7. The conductive device of claim 1, wherein the graphene film is doped in order to reduce its surface resistance.

8. The conductive device of claim 1, wherein the graphene film is doped with P-dopants.

9. The conductive device of claim 1, wherein the graphene film is doped with P-dopants chosen among $AuCl_3$ and $HNO_3$.

10. The conductive device of claim 1, wherein the conductive device comprises either one graphene film or more than one graphene films, wherein layers of $FeCl_3$ intercalated between the more than one graphene films.

11. The conductive device of claim 1, wherein said polymer material comprises a polymer from a n-xylylene family.

12. The conductive device of claim 1, wherein said polymer from the n-xylylene family is parylene.

13. The conductive device of claim 1, wherein the polymer material forms a layer of between 5 and 40 nm in thickness.

14. The conductive device of claim 1, wherein the conductive device is a conductive medical device.

15. The conductive device of claim 14, wherein said conductive medical device is a conductive medical patch, a wound treatment apparatus, an ophthalmic element, an eye protection device or an implant.

16. The conductive device of claim 14, wherein the conductive medical device is a conductive medical patch and further comprises:
an adhesive band covering the support and holding the graphene film in contact with a body of an animal or a human, wherein the adhesive band is removable from the body; and
at least one wire contact electrically coupled to the graphene film.

17. The conductive device of claim 16, wherein the polymer material comprises hyaluronic acid.

18. The conductive device of claim 16, wherein the conductive medical patch is a hydrocolloidal dressing, the graphene film forming an external surface for contact with wound, and the polymer material being a porous layer positioned between the graphene film and a pad formed of a hydrocolloid.

19. A wound treatment apparatus comprising two conductive medical patches according to claim 16, each of said two conductive medical patches being placed over the wound and comprising:
the graphene film;
the support for the graphene film, the support comprising the layer of polymer material covering a surface of the graphene film;
the adhesive band covering the support, the adhesive band holding the graphene film in contact with the body of the animal or the human, wherein the adhesive band is removable from the body;
a first and a second electrode, each of said electrodes being electrically coupled to the graphene film of each of said two conductive medical patches; and
a voltage application module adapted to apply voltage pulses between the first and the second electrodes.

20. A wound treatment apparatus comprising two conductive medical patches according to claim 16, one of the two conductive medical patches for placing over the wound; each of the two conductive medical patches comprising:
the graphene film;
the support for the graphene film, the support comprising the layer of polymer material covering the surface of the graphene film;
the adhesive band covering the support, the adhesive band for and holding the graphene film in contact with the body of the animal or the human, wherein the adhesive band is removable from the body;

a wire contact electrically coupled to the graphene film; and a voltage application module adapted to apply voltage pulses between the two conductive medical patches.

21. The wound treatment apparatus according to claim 19, further comprising a wound dressing portion for covering a wound, an electrode patch for electrical contact with the body, and a current sensor and/or voltage sensor for detecting current and/or voltage applied between the wound dressing portion and the electrode patch.

22. The wound treatment apparatus according to claim 19, further comprising a wound dressing portion for covering a wound, an electrode patch for electrical contact with the body, and a pulse generator for detecting current and/or voltage applied between the wound dressing portion and the electrode patch.

23. The conductive device according to claim 14, wherein the conductive medical device is an ophthalmic element comprising a curved plate formed of the graphene film covered by the polymer material which forms an outer layer, wherein a substrate on which the graphene film is formed has a curved surface with a shape compatible with a surface of an eye.

24. An eye protection device comprising the ophthalmic element of claim 23, wherein the graphene film forms a continuous layer across the ophthalmic element.

25. The conductive device according to claim 14, wherein the conductive medical device is an implant, said implant comprising:

a core in a form of a shaft having a pointed end and formed of the polymer material; and the graphene film covering and supported by the polymer core, wherein a substrate on which the graphene film is formed is a mold having an inner surface having the form of the implant, and wherein the graphene film is deposited on the inner surface of the mold, the mold is filled by the polymer material to form the polymer core of the implant that supports the graphene film.

26. An implant according to claim 25, wherein a first portion of said mold is removed during formation of the implant, so that a second portion of said mold remains in contact with the graphene film and forms an electrode of the implant.

27. A method for monitoring wound healing using a conductive device according to claim 16.

* * * * *